United States Patent
Herigstad et al.

(10) Patent No.: US 9,249,182 B2
(45) Date of Patent: *Feb. 2, 2016

(54) PURIFICATION OF ANTIBODIES USING HYDROPHOBIC INTERACTION CHROMATOGRAPHY

(71) Applicant: ABBVIE INC., North Chicago, IL (US)

(72) Inventors: Matthew Omon Herigstad, Charlestown, MA (US); Linda E. Rich, Worcester, MA (US); Stephen Ming-teh Lu, Worcester, MA (US); Natarajan Ramasubramanyan, Westborough, MA (US)

(73) Assignee: AbbVie, Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/831,181

(22) Filed: Mar. 14, 2013

(65) Prior Publication Data

US 2014/0072585 A1 Mar. 13, 2014

Related U.S. Application Data

(60) Provisional application No. 61/651,544, filed on May 24, 2012, provisional application No. 61/658,920, filed on Jun. 13, 2012.

(51) Int. Cl.
| | |
|---|---|
| *C07K 1/22* | (2006.01) |
| *C07K 16/00* | (2006.01) |
| *C07K 1/20* | (2006.01) |
| *C07K 1/36* | (2006.01) |
| *C07K 16/24* | (2006.01) |
| *B01D 15/32* | (2006.01) |

(52) U.S. Cl.
CPC ............... *C07K 1/22* (2013.01); *B01D 15/327* (2013.01); *C07K 1/20* (2013.01); *C07K 1/36* (2013.01); *C07K 16/00* (2013.01); *C07K 16/241* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,096,816 A | 3/1992 | Maiorella |
| 5,110,913 A | 5/1992 | Coan et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |

(Continued)

FOREIGN PATENT DOCUMENTS

| | | |
|---|---|---|
| CN | 1299370 A | 6/2001 |
| CN | 1563090 A | 1/2005 |

(Continued)

OTHER PUBLICATIONS

Liu et al. "Recovery and purificaiton process development for monoclonal antibody production" mAbs 2(5), 2010, pp. 480-499.*
"Genentech unveils production capacity hikes," in-Pharma Technologist.com Jun. 28, 2005, pp. 1-2.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS.
"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS.

(Continued)

*Primary Examiner* — Daniel E Kolker
*Assistant Examiner* — James Rogers
(74) *Attorney, Agent, or Firm* — McCarter & English, LLP; Maria Laccotripe Zacharakis; Maneesh Gulati

(57) ABSTRACT

Disclosed herein are compositions and methods for purifying antibody products from a sample matrix. In particular, the present invention relates to compositions and methods for purifying antibody products employing hydrophobic interaction chromatography media. In certain embodiments, the invention provides a method for reducing process-related impurities (e.g., host cell proteins), as well as product-related substances, including molecular weight variants (e.g., aggregates and fragments of the antibody product).

45 Claims, 7 Drawing Sheets

(56) References Cited

U.S. PATENT DOCUMENTS

| | | |
|---|---|---|
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,673,986 B1 | 1/2004 | Kucherlapati et al. |
| 6,680,181 B1 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,974,681 B1 | 12/2005 | McGrew |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,323,553 B2 | 1/2008 | Fahrner et al. |
| 7,332,303 B2 | 2/2008 | Schilling et al. |
| 7,390,660 B2 | 6/2008 | Behrendt et al. |
| 7,429,491 B2 | 9/2008 | Luan et al. |
| 7,504,485 B2 | 3/2009 | Salfeld et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,034,906 B2 | 10/2011 | Borhani et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,231,876 B2 | 7/2012 | Wan et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,552 B2 | 6/2013 | Croughan et al. |
| 8,663,945 B2 | 3/2014 | Pla et al. |
| 8,753,633 B2 | 6/2014 | Salfeld et al. |
| 8,821,865 B2 | 9/2014 | Neu et al. |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 9,017,687 B1 | 4/2015 | Wang et al. |
| 9,062,106 B2 | 6/2015 | Bengea et al. |
| 9,067,990 B2 | 6/2015 | Wang at al. |
| 9,085,618 B2 | 7/2015 | Ramasubramanyan et al. |
| 9,085,619 B2 | 7/2015 | Fraunhofer et al. |
| 9,090,688 B2 | 7/2015 | Bengea et al. |
| 2002/0045207 A1 | 4/2002 | Krummen et al. |
| 2002/0132299 A1 | 9/2002 | Field |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |

(56) References Cited

U.S. PATENT DOCUMENTS

| | | |
|---|---|---|
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0153846 A1 | 7/2006 | Krause et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0041905 A1 | 2/2007 | Hoffman et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1* | 11/2009 | Fraunhofer et al. ......... 424/85.5 |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0172911 A1 | 7/2010 | Naso et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmller et al. |
| 2012/0039908 A1 | 2/2012 | Combs et al. |
| 2012/0077213 A1 | 3/2012 | Pla et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0244280 A1 | 9/2013 | Parikh et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |

(56) References Cited

U.S. PATENT DOCUMENTS

| | | |
|---|---|---|
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0275494 A1 | 9/2014 | Wang et al. |
| 2014/0288278 A1 | 9/2014 | Nti-Gyabaah et al. |
| 2014/0301977 A1* | 10/2014 | Nadarajah et al. .......... 424/85.2 |
| 2014/0314745 A1 | 10/2014 | Rives et al. |
| 2014/0377275 A1 | 12/2014 | Neu at al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |
| 2015/0132320 A1 | 5/2015 | Chumsae et al. |
| 2015/0132801 A1 | 5/2015 | Ramasubramanyan et al. |
| 2015/0140006 A1 | 5/2015 | Ramasubramanyan et al. |
| 2015/0141632 A1 | 5/2015 | Markosyan |
| 2015/0158944 A1 | 6/2015 | Bengea et al. |
| 2015/0166650 A1 | 6/2015 | Ramasubramanyan et al. |
| 2015/0166653 A1 | 6/2015 | Wang et al. |
| 2015/0183865 A1 | 7/2015 | Rives et al. |
| 2015/0183866 A1 | 7/2015 | Rives et al. |

FOREIGN PATENT DOCUMENTS

| | | |
|---|---|---|
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 0351789 A2 | 1/1990 |
| EP | 0366043 A1 | 5/1990 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2357250 A2 | 8/2011 |
| EP | 2495307 A1 | 9/2012 |
| EP | 2528002 A2 | 11/2012 |
| EP | 2574677 A1 | 4/2013 |
| GB | 2160530 A | 12/1985 |
| GB | 2279077 A | 12/1994 |
| IN | 2285/MUM/2013 A1 | 1/2015 |
| JP | 7289288 A | 11/1995 |
| WO | WO-98-23645 A1 | 0/1998 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/09967 A1 | 7/1991 |
| WO | WO-92/01047 A1 | 1/1992 |
| WO | WO-92/11383 A1 | 7/1992 |
| WO | WO-92/16553 A1 | 10/1992 |
| WO | WO-93/06213 A1 | 4/1993 |
| WO | WO-94/02602 A1 | 2/1994 |
| WO | WO-94/08619 A1 | 4/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-9704801 A1 | 2/1997 |
| WO | WO-97/13852 A1 | 4/1997 |
| WO | WO-97/29131 A1 | 8/1997 |
| WO | WO-98/24883 A2 | 6/1998 |
| WO | WO-98/24884 A1 | 6/1998 |
| WO | WO-98/24893 A2 | 6/1998 |
| WO | WO-9823645 A1 | 6/1998 |
| WO | WO-98/50433 A2 | 11/1998 |
| WO | WO-9856418 A1 | 12/1998 |
| WO | WO-99/32605 A1 | 7/1999 |
| WO | WO-99/57134 A1 | 11/1999 |
| WO | WO-9957246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-01077362 A1 | 10/2001 |
| WO | WO-02/12502 A2 | 2/2002 |
| WO | WO-0212501 A2 | 2/2002 |
| WO | WO-03045995 A2 | 6/2003 |
| WO | WO-03/059935 A2 | 7/2003 |
| WO | WO-03/066662 A2 | 8/2003 |
| WO | WO-2004008100 A2 | 1/2004 |
| WO | WO-04/058944 A2 | 7/2004 |
| WO | WO-2004/058944 A2 | 7/2004 |
| WO | WO-2004058800 A2 | 7/2004 |
| WO | WO-2004/097006 A1 | 11/2004 |
| WO | WO-2005042569 A1 | 5/2005 |
| WO | WO-2005-062967 A2 | 7/2005 |
| WO | WO-2005/082483 A1 | 9/2005 |
| WO | WO-2006/043895 A2 | 4/2006 |
| WO | WO-2006045438 A1 | 5/2006 |
| WO | WO-2006/099308 A2 | 9/2006 |
| WO | WO 2006099308 A2 * | 9/2006 |
| WO | WO-2006/110277 A1 | 10/2006 |
| WO | WO-2007/087384 A2 | 8/2007 |
| WO | WO-2007/117490 A2 | 10/2007 |
| WO | WO-2008/033517 A2 | 3/2008 |
| WO | WO-2008-057240 A2 | 5/2008 |
| WO | WO-2008068879 A1 | 6/2008 |
| WO | WO-2008087184 A2 | 7/2008 |
| WO | WO-2008121616 A2 | 10/2008 |
| WO | WO-2008135498 A2 | 11/2008 |
| WO | WO-2009/017491 A1 | 2/2009 |
| WO | WO-2009023562 A2 | 2/2009 |
| WO | WO-2009/027041 A1 | 3/2009 |
| WO | WO-2009058769 A1 | 5/2009 |
| WO | WO-2009/073569 A2 | 6/2009 |
| WO | WO-2009135656 A1 | 11/2009 |
| WO | WO-2010036443 A1 | 4/2010 |
| WO | WO-2010043703 A1 | 4/2010 |
| WO | WO-2010122460 A1 | 10/2010 |
| WO | WO-2010/129469 A1 | 11/2010 |
| WO | WO-2010127069 A1 | 11/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |

(56) References Cited

FOREIGN PATENT DOCUMENTS

| WO | WO-2011098526 A1 | 8/2011 |
|---|---|---|
| WO | WO-2011110598 A1 | 9/2011 |
| WO | WO-2011/133886 A2 | 10/2011 |
| WO | WO-2011127322 A1 | 10/2011 |
| WO | WO-2011134919 A2 | 11/2011 |
| WO | WO-2011134920 A1 | 11/2011 |
| WO | WO-2012019160 A1 | 2/2012 |
| WO | WO-2012030512 A1 | 3/2012 |
| WO | WO-2012/046255 A2 | 4/2012 |
| WO | WO-2012050175 A1 | 4/2012 |
| WO | WO-2012051147 A1 | 4/2012 |
| WO | WO-2012/065072 A2 | 5/2012 |
| WO | WO-2012062810 A2 | 5/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013/011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-164837 A1 | 11/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |
| WO | WO-2013-186230 A1 | 12/2013 |
| WO | WO-2014/039903 A2 | 3/2014 |
| WO | WO-2014/099636 A1 | 6/2014 |
| WO | WO-2014/207763 A1 | 12/2014 |
| WO | WO-2015/004679 A1 | 1/2015 |
| WO | WO-2015/007912 A1 | 1/2015 |

OTHER PUBLICATIONS

"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS.

"Memorandum in Support of Centocor's Motion No. 3 for Summary Judgment that the 394 and 031 Patents Are Invalid for Under 35 U.S.C. §102(f) for Failing to Name the Proper Inventors", dated Aug. 1, 2013 and submitted by defendant in Civil Action No. 09-40089-FDS.

"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS.

"Plaintiffs' Memorandum in Support of Their Motion for Partial Summary Judgment", dated Aug. 1, 2013 and submitted by plaintiff in Civil Action No. 09-40089-FDS.

"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS.

Abraham, E., et al., "Efficacy and Safety of Monoclonal Antibody to Human Tumor Necrosis Factor α in Patients with Sepsis Syndrome," *JAMA*, vol. 273(12):934-941 (1995).

Adams. et al. J. Am. Acad. Dermatol 2004;51 :660-2.

Altamirano, C., et al., "Strategies for fed batch cultivation of t-PA producing CHO cells: substitution of glucose and glutamine and rational design of culture medium", *J. Biotechn.* 110:171-179, 2004.

Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.

Avgerinos et al. (GAb '04 Abstracts—GE Healthcare Life Sciences, France Oct. 3-5, 2004, pp. 15-16 published 2005).

Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.

Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.

Barbuto, J. et al. "Production of Neutralizing Antibodies to Tumor Necrosis Factor by Human Tumor-Infiltrating B Lymphocytes" *Proc. Am. Assoc. Cancer Res*,. 34:487, Abstr. 2904 (1993).

Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).

Biblia, T.A. et al., "In Pursuit of the Optimal Fed-Batch Process for Monoclonal Antibody Production", Biotechnol. Prog 11(1):1-13, Jan.-Feb. 1995.

Birch, Jr. et al., "Antibody production", Adv. Drug Delivery Reviews 58:671-685, 2006.

Blaker, GJ, et al., "The Glucose, Insulin and Glutamine Requirements of Suspension Cultures of HeLa Cells in a Defined Culture Medium", J. Cell Sci. 9:529-537, 1971.

Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).

Bollati-Fogolin M., et al., "Temperature Reduction in Cultures of hGM-CSF-expressing CHO Cells: Effects on Productivity and Product Quantity", Biotechnol. Prog. 21:17-21, 2005.

Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.

Boswell et al. "Effects of Charge on Antibody Tissue Distribution and Pharmacokinetics" Bioconjugate Chem.(21) 2153-2163 (2010).

Boyle, P. et al. "A Novel Monoclonal Human IgM Autoantibody which Binds Recombinant Human and Mouse Tumor Necrosis Factor-α" *Cell. Immunol.*, 152:556-68 (1993).

Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).

Brekke, O. et al., "Therapeutic Antibodies for Human Diseases at the Dawn of the Twenty-first Century," Nature, vol. 2:52-62 (2002).

Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).

Bruggemann et al., "Production of human antibody repertoires in transgenic mice" Cur. Op. Biotechnol. 455-458 (1997).

Bruggemann, M., Neuberger, M.S., "Strategies for expressing human antibody repertoires in transgenic mice," *Immunol. Today* 17:391-397 (1996).

Cai B, et al. "C-Terminal Lysine Processing of Human Immunoglobulin G2 Heavy Chain in Vivo" Biotechnol. Bioeng. 108: 404-412 (2011).

Cambridge Antibody Technology, advertisement of phage display services, Science vol. 253, No. 5018 (1991).

Carter et al., "Humanization of an anti-p185HER2 antibody for human cancer therapy," *Proc. Nat. Acad. Sci* 89:4285-4289 (1992).

Chang KH, et al., "N-Acetylcysteine Increases the Biosynthesis of Recombinant EPO in Apoptotic Chinese Hamster Ovary Cells", Free Radic Res. 30(2):85-91, 1999.

Charter, Edward A., "A New Process for the Separation and Purification of Egg Yolk; Antibodies," BASc., The University of British Columbia; A Thesis; Apr. 1993.

(56) References Cited

OTHER PUBLICATIONS

Choo et al. "High-level production of a monoclonal antibody in murine myeloma cells by perfusion culture using a gravity settler" Biotechnology Progress, vol. 23, No. 1, Jan. 1, 2007, 225-231.

Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).

Chua, FKF et al., "Hyper-stimulation of monoclonal antibody production by high osmolarity stress in eRDF medium", J. Biotechnology 37(3):265-275, Nov. 15, 1994.

Chung et al., "Utilization of Lysozyme Charge Ladders to Examine the Effects of Protein Surface; Charge Distribution on Binding Affinity in Ion Exchange Systems," Langmuir 26(2): 759-768 (2010).

Chung et al., "Cetuximab-Induced Anaphylaxis and IgE Specific for Galactose-α-1, 3-Galactose", *N. Engl. J. Med.*, 358:11, pp. 1109-1117 (2008).

Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).

Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).

Cox, J. et al. "A directory of human germ-line Vk segments reveals a strong bias in their usage" *Eur. J. Immunol.*, 24(2):827-36 (1994).

Cromwell (GAB'04 Abstracts—GE Healthcare Life Sciences, Franc Oct. 3-5, 2004, pp. 17-18 published 2005).

Daugherty, et al. Formulation and Delivery Issues for Monoclonal Antibody Therapeutics. Advanced Drug Delivery Reviews, 2006. vol. 58, pp. 686-706.

Davies et al., "Antibody VH domains as small recognition units." *Biotechnology*, 13:475-479 (1995).

Department of Surgery, University of Toronto, Annual Report (1998-1999)(348 pages).

DePhillips et al., "Determinants of protein retention characteristics on cation-exchange adsorbents,"; Journal of Chromatograph A, 933:57-72 (2001).

deZongotita et al., "Phosphate feeding improves high-cell-concentration NS0 myeloma cell culture performance for monoclonal antibody production" Biotechnology and Bioengineering. 2000, 69: 566-576.

Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143;.

Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).

Doring, E., "Identification and Characterization of a TNFa Antagonist Derived from a Monoclonal Antibody" (1994) *Mol. Immunol* .31(14): 1059-1067.

Elliot et al., "Repeated therapy with monoclonal antibody to tumour necrosis factor α (cA2) in patients with rheumatoid arthritis" (1994) *Lancet*, 344:1125-1127.

Elliot, "Treatment of rheumatoid arthritis with chimeric monoclonal antibodies to tumor necrosis factor α" (1993) *Arthritis & Rheumatism*, 36(12):1681-1690.

Erbitux (cetuximab) label, Revised Aug. 2013.

Ewert et al., "Biophysical Properties of Human Antibody Variable Domains," J. Mol. Biol. 324: 531-; 553 (2003).

Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*.

Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.n.Y.

Exhibit dated Aug. 1, 2013 and cited by plaintiff in Civil Action No. 09-40089-FDS providing excerpts from the File History of U.S. Appl. No. 12/578,487.

Exhibit dated Aug. 1, 2013 and cited by defendant in Civil Action No. 09-40089-FDS providing the Jun. 24, 2009 trial transcript of the AM session in the matter of *Centocor, et al.* v. *Abbott Laboratories*, E.D. TX.

Exhibit dated Aug. 1, 2013 and cited by defendant in Civil Action No. 09-40089-FDS providing the Sep. 20, 2012 Day 8 trial transcript in the matter of *Abbott* v. *Centocor Ortho Biotech Inc.*, D. MA.

Exhibit dated Aug. 1, 2013 and cited by plaintiff in Civil Action No. 09-40089-FDS providing Declaration by Jochen Salfeld, dated Jan. 17, 2013.

FDA Package insert for Adalimumab, Sep. 26, 2003, pp. 1-18.

Feldmann, "Anti-TNF-alpha Therapy of Rheumatoid Arthritis: What Have We Learned?" (2001) *Annu. Rev. Immunol.*, 19:163-196.

Figini, "In Vitro assembly of Repertoires of Antibody Chains on the Surface of Phage by Renaturation" (1994) *J. Mol. Biol.*, 239:68-78.

Fishwild et al., "High-avidity human IgG kappa monoclonal antibodies from a novel strain of minilocus transgenic mice" (1996) *Nature Biotechnology*, 14:845-851.

Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.

Foote, J., "Antibody framework residues affecting the conformation of the hypervariable loops" (1992) *J. Mol .Biol.*, 224(2):487-499.

Freitag et al., "Displacement chromatography in biotechnological downstream processing," J. Chromatography, (1995) 691(1):101-112.

Gagnon et al., "A Systematic Approach to the Purification of Monoclonal Antibodies," *LC-GC* 11 (1):26-34 (1993).

Gatto, B. "Biologics targeted at TNF: design, production and challenges", Reumatismo 58(2):94-103, 2006.

Genbank Entry for CHO Cathepsin L., EGW13555, Aug. 25, 2011, pp. 1-2.

Ghaderi, et al., "Implications of the Presence of N-glycolylneuraminic acid in Recombinant Therapeutic Glycoproteins", *Nature Biotechnology*, 28(8):863-868 (2010).

Ghaderi, et al., "Production platforms for biotherapeutic glycoproteins. Occurrence, impact, and challenges of non-human sialylation", *Biotechnology and Genetic Engineering Reviews*, 28:147-176 (2012).

Gonzalez et al. "Purification of Lactic Acid from Fermentation Broths by Ion-Exchange Resins" Ind. Eng. Chem. Res. 45:3243 (2006).

Graf et al., "Ion exchange resins for the purification of monoclonal antibodies from animal cell culture" Bioseparation 4 (1) :7-20 (Feb. 1994). ;4 (1) :7-20 (Feb. 1994).

Gram et al., "In vitro selection and affinity maturation of antibodies from a naive combinatorial immunoglobulin library" (1992) *PNAS*, 89:3576-3580.

Gramer et al., "Glycosidase Activities of the 293 and NS0 Cell Lines, and of an Antibody-Producing Hybridoma Cell Line", *Biotechnology and Bioengineering*, 43:423-428 (1994).

Green et al., "Antigen-specific human monoclonal antibodies from mice engineered with human Ig heavy and light chain YACs" (1994) *Nature Genetics*, 7:13-21.

Griffiths et al., "Isolation of high affinity human antibodies directly from large synthetic repertoires" (1994) *EMBO J.*, 13:3245-3260.

Griffiths, "Human anti-self antibodies with high specificity from phage display libraries" (1993) *The EMBO J.* 12(2):725-34.

Grunberg, J. et al., "High-Yield Production of Recombinant Antibody Fragments in HEK-293 Cells Using Sodium Butyrate", BioTechniques 34(5):968-972, May 2003.

Han, Kyu Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.

Harlow and Lane, Antibodies A Laboratory Manual, Purification of Antibodies by using a; Deae-matrix (Batch), Storing and Purifying Antibodies; Chapter 8: 302-303 (1988).

(56) References Cited

OTHER PUBLICATIONS

Harris et al. "Processing of C-terminal lysine and argnine residues of proteins isolated from mammalian cell culture" Journal of Chromatography, (1995) 705; 129-123.
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hokke et al., "Sialylated Carbohydrate Chains of Recombinant Human Glycoproteins Expressed in Chinese Hamster Ovary Cells Contain Traces of N-glycolylneuraminic acid", *FEBS*,275:9-14 (1990).
Holler, "Modulation of Acute Graft-Versus-Host Disease After Allogeneic Bone Marrow Transplantation by Tumor Necrosis Factor -alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(1 1):484-490 (2003).
Hoogenboom et al., "By-passing immunisation : Human antibodies from synthetic repertoires of germline VH gene segments rearranged in vitro" (1992) *J. Mol. Biol.*, 227:381388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206;.
http://www.cygnustechnologies.com/product_detail/host-cell-protein-antibodies/anti-cho-h . . . Cygnus Technologies, Anti-CHO HCP (Apr. 18, 2012).
Huang et al. "Effects of anti-TNF monoclonal antibody infusion in patients with hairy cell leukaemia" (1992) *Br. J. Haematol.*, 81(2):231-234.
Hui et al., "Recovery and purification process development for monoclonal antibody production," MABS (2010) 2(5):480-499.
Humira (adalimumab) label, Revised Sep. 2013.
Huse, "Generation of a large combinatorial library of the immunoglobulin repertoire in phage lambda" (1989) *Science*, 246:1275-81.
International Preliminary Report on Patentability for Application No. PCT/US07/08359, dated Dec. 12, 2011.
International Preliminary Report on Patentability for Application No. PCT/US2011/060388, dated May 30, 2012.
International Search Report and Written Opinion for Application No. PCT/US2008/085066, dated May 12, 2009.
International Search Report and Written Opinion for Application No. PCT/US2010/033387, dated Aug. 7, 2012.
International Search Report and Written Opinion for Application No. PCT/US2013/031380, dated Feb. 5, 2014.
International Search Report and Written Opinion for Application No. PCT/US2013/041954, dated Dec. 17, 2013.
International Search Report and Written Opinion for Application No. PCT/US2013/041958, dated Dec. 17, 2013.
International Search Report and Written Opinion for Application No. PCT/US2013/065720, dated Dec. 16, 2013.
International Search Report and Written Opinion for Application No. PCT/US2013/065797, dated Nov. 26, 2013.
International Search Report for Application No. PCT/IB03/04502, dated May 26, 2004.
International Search Report for Application No. PCT/US2011/060388 dated May 30, 2012.
International Search Report for Application No. PCT/US2013/031352, Dated Apr. 25, 2013.
International Search Report for Application No. PCT/US2013/031389, Dated Jun. 3, 2013.
International Search Report for Application No. PCT/US2013/031485, Dated Jun. 25, 2013.
International Search Report for Application No. PCT/US2013/031681, Dated Jun. 14, 2013.
Invitation to Pay Additional Fees for International Application No. PCT/US2013/031380, Dated Nov. 28, 2013.
Jakobovits, A., "Production of fully human antibodies by transgenic mice" (1995) *Curr. Op. Biotechnol.*, 6:561-566.
Jespers, "Guiding the Selection of Human Antibodies from Phage Display Repertoires to a Single Epitope of an Antigen" (1994) *Bio/Technology*, 12:899-903.
Johnson et al. (Archives of Biochemistry and Biophysics 444 (2005) 7-14).
Kalyanpur, M., "Downstream Processing in the Biotechnology Industry" Molecular Biotechnology, vol. 22:87-98 (2002).
Karampetsou et al. (Q J Med 2010; 103:917-928).
Kaschak et al: "Characterization of the basic charge variants of a human IgGI: Effect of copper concentration in cell culture media", MABS, vol. 3, No. 6, Nov. 1, 2011, pp. 577-583,.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor -alpha monoclonal antibody" (2000) *Ann. Rheum. Dis.*, 59(Suppl.1):1 44-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp.; 613-624;.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatography, 266:3-21 (1983).
Lerner, "Antibodies without immunization" (1992) *Science*, 258:1313-1314.
Lewis, "Use of alanine scanning mutagenesis to improve the affinity of an anti gp120 (HIV) antibody" (1994) *J. Cell. Biochem.*, 18D:215.
Li, F. et al., "Current Therapeutic Antibody Production and Process Optimization" BioProcessing Journal, vol. 4(5):23-30 (2005).
Lifely et al., "Glycosylation and Biological Activity of CAMPATH-1 H Expressed in Different Cell Lines and Grown Under Different Culture Conditions", *Glycobiology*, 5(8):813-822 (1995).
Logan, John S. "Transgenic Animals: Beyond 'Funny Milk'", *Current Opinion in Biotechnology*, 4:591-595 (1993).
Lonberg et al., "Antigen-specific human antibodies from mice comprising four distinct genetic modifications" (1994) *Nature*, 368:856-859.
Lonberg et al., "Human Antibodies from Transgenic Mice" (1995) *Int. Rev. Immunol.*, 13:65-93.

(56) References Cited

OTHER PUBLICATIONS

Low, "Mimicking Somatic Hypermutation: Affinity Maturation of Antibodies Displayed on Bacteriophage Using a Bacterial Mutator Strain" (1996) *J. Mol. Biol.*, 260:359-368.
Low, Nigel: thesis extract (1996) *Cambridge University*.
Luo et al., "Understanding of C-terminal lysine variants in antibody production using mammalian cells" Abstract of papers, ACS, Anaheim, CA, US, Mar. 2011.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Ma, et al., "Generation and Assembly of Secretory Antibodies in Plants", *Science*, 268:716-719 (1995).
Maeda, et al., "Analysis of Nonhuman N-Glycans as the Minor Constituents in Recombinant Monoclonal Antibody Pharmaceuticals", *Anal. Chem.*, 84:2373-2379 (2012).
Mahler, et al. Induction and analysis of aggregates in a liquid IgG1-antibody formulation. Eur J Pharm Biopharm. 2005, 59(3):407-17; pg. 408; col. 1-2; p. 409; col. 2, "2.2.2 Stirring stress".
Marks et al., "Human antibody fragments specific for human blood group antigens from a phage display library" (1993) *Bio/Technology*, 11:1145-1150.
Marks et al., "Molecular evolution of proteins on filamentous phage. Mimicking the strategy of the immune system" (1992) *J. Biol. Chem.* 267:16007-16010.
Marks, "By-passing immunization: Human antibodies from V-gene libraries displayed on phage" (1991) J. Mol. Biol., 222:581-597.
Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.
Marks, JD., "By-Passing Immunization: Building High Affinity Human Antibodies by Chain Shuffling" (1992) *Biotechnology*, 10:779-783.
Martin, A.C.R. "Accessing the Kabat antibody sequence database by computer" (1996)*Proteins: Structure, Function and Genetics*, 25:130-133.
Medynski, "Phage Display: All Dressed Up and Ready to Role" (1994) *Bio/Technology*, 12:1134-1136.
Mendez et al., "Functional transplant of megabase human immunoglobulin loci recapitulates human antibody response in mice" (1997) *Nature Genetics*, 15:146-156.
Meuwly, F. et al., "Conversion of a CHO cell culture process from perfusion to fed-batch technology without altering product quality", J.Biotechn. 123:106-116, 2006.
Miller et al. "Characterization of site-specific glycation during process development of a human therapeutic monoclonal antibody" Journal of Pharmaceutical Sciences, vol. 100, No. 7, Jul. 2011, 2543-2550.
Millipore, "Pellicon 2 Filters and Holders," 2003, pp. 1-8.
Moore, A., et al., "Effects of temperature shift on cell cycle, apoptosis and nucleotide pools in CHO cell batch cultures", Cytotechnology, 23:47-54, 1997.
Möller, Monoclonal antibodies to human tumor necrosis factor α: in vitro and vivo application (1990) *Cytokine*, 2(3):162-69.
Neuberger M. et al., "Mice perform a human repertoire" (1997) *Nature*, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Nilsson, "Antibody engineering" (1995) *Current Opinion in Structural Biology*, 5:450-456.
Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron*, 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).
Oh, D-K. et al., "Increased erythritol production in fed-batch cultures of *Torula* sp. By controlling glucose concentration", J. Industrial Microb. & Biotechn. 26(4): 248-252, 2001.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) *Methods*, 36(1):61-68.
Perchiacca et al., "Aggregation-resistance domain antibodies engineered with charged mutations; near the edges of the complementarity-determining regions," Protein Engineering Design & Selection, 25:10 (591-601) 2012.
Pietersz et al., "In vitro and in vivo Antitumor Activity of a Chimeric anti-CD19 Antibody", *Cancer Immunol. Immunother.*, 41:53-60 (1995).
Potter et al., "Antibody Production in the Baculovirus Expression System", *Intern. Rev. Immunol.*, 10:103-112 (1993).
Poul et al., "Design of Cassette Baculovirus Vectors for the Production of Therapeutic Antibodies in Insect Cells", *Immunotechnology*, 1:189-196 (1995).
Queen, C., "A humanized antibody that binds to the interleukin 2 receptor" (1989) *Proc. Natl. Acad. Sci. USA*, 86(24):10029-10033.
Rader et al. "A phage display approach to rapid antibody humanization: Designed combinatorial V gene libraries" (1998) *Proc Natl Acad Sci USA*, 95:8910-8915.
Raju, TS. "Glycosylation Variations with Expression Systems and Their Impact on Biological Activity of Therapeutic Immunoglobulins", *BioProcess International*., 44-53 (2003).
Reichert JM., et al., "Monoclonal antibody successes in the clinic", Nature Biotech. 23(9):10731078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in *Yeast Pichia pastoris*", *Biotechnology*, 13:255-260 (1995).
Riechmann, "Phage display and selection of a site-directed randomized single-chain antibody Fv fragment for its affinity improvement" (1993) *Biochemistry*, 32(34):8848-8855.
Rube et al. (Int. J. Radiation Oncology Biol. Phys., vol. 56, No. 5, pp. 1414-1425,2003).
Rudikoff et al., "Single amino acid substitution altering antigen-binding specificity" (1982) *Proc. Natl. Acad. Sci. USA*, 70:1979-1983.
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.
Santora et al., "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.
Sato et al, "Stimulation of monoclonal antibody production by human-human hybridoma cells with an elevated concentration of potassium or sodium phosphate in serum-free medium," Cytotechnology 2:63-67, 1989.

(56) References Cited

OTHER PUBLICATIONS

Schiestl et al. "Acceptable changes in quality attributes of glycosylated biopharmaceuticals" Nature Biotechnology, 29(4), 310-312 (2011).

Schwieterman, "Immunosuppression in Combination with Monoclonal Antibodies" in Biologic Agents in Autoimmune Disease (Mar. 2-4, 1995).

Senczuk et al. "Hydrophobic interaction chromatography in dual salt system increases protein binding capacity" Biotechnology and Bioengineering, 103(5), 2009.

Seresht et al., "The impact of phosphate scarcity on pharmaceutical protein production in *S. cerevisiae*: linking transcriptomic insights to phenotypic responses" Microbial Cell Factories. 2011, 10: 104.

Sheeley et al., "Characterization of Monoclonal Antibody Glycosylation: Comparison of Expression Systems and Identification of Terminal α-Linked Galactose", *Anal. Biochem.*, 247(1):102-110 (1997).

Sheikh et al., "Studies of the digestion of bradykinin, lysyl bradykinin, and kinin-degradation products by carboxypeptidases A, B, and N;". Biochemical Pharmacology. 1986, 35: 1957-1963.

Shih, "Effects of Anions on the Deamidation of Soy Protein". Journal of Food Science. 1991, 56: 452-454.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Takagi, M. et al., "The effect of osmolarity on metabolism and morphology in adhesion and suspension chinese hamster ovary cells producing tissue plasminogen activator", Cytochnology 32:171-179, 2000.

Tamura et al., "Structural correlates of an anticarcinoma antibody: identification of specificity-determining residues (SDRs) and development of a minimally immunogenic antibody variant by retention of SDFs only," *J. lmmun.* (2000) 164:1432-1441.

Tan et al. (Biotechnol. Appl. Biochem. (1999) 30, 59-64).

Taylor et al., "Human immunoglobulin transgenes undergo rearrangement, somatic mutation and class switching in mice that lack endogenous IgM" (1994) *Int. Immunol.*, 6:579-591.

Teichmann, S. Declaration dated Dec. 7, 2010 from opposition proceedings in EP 0929578.

The MW Calculator available at the Sequence Manipulation Suite (see http://bioinformatics.org/sms2/index.html), downloaded Feb. 25, 2014.

The pI Calculator available at the Sequence Manipulation Suite (see <http://bioinformatics.org/sms2/index.html>), downloaded Feb. 25, 2014, p. 1).

The Statement on a Nonproprietary Name Adopted by the USAN Council for Adalimumab, p. 1, downloaded on May 19, 2011 from http://www.ama-assn.org/resources/doc/usan/adalimumab.doc.

Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.

Tomiya et al., "Comparing N-glycan processing in mammalian cell lines to native and engineered; lepidopteran insect cell lines," Glycoconjuqate Journal 21:343-360 (2004).

Tomlinson, "The repertoire of human germline VH sequences reveals about fifty groups of VH segments with different hypervariable loops" (1992) *J. Mol. Biol.*, 227:776-98.

Tomlinson, "The structural repertoire of the human Vk domain" (1995) *The EMBO J.*, 14(18):4628-38.

Tracey, "Tumor necrosis factor: A pleiotropic cytokine and therapeutic target" (1994) *Annu. Rev. Med.*, 45:491-503.

Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:1 601 2-1 6022 (2010).

Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.

Van Lent PL, et al. "The impact of protein size and charge on its retention in articular cartilage" J Rheumatol. Aug. 1987;14(4):798-805.

Varasteh et al. Optimization of Anti-Rh D Immunoglobulin Stability in the Lyphiliization Process. Iranian Journal of Basic Medical Sciences, Spring 2008, vol. 11, No. 1. pp. 55-61.

Vaughan, "Human antibodies by design" (1998) *Nature Biotechnology*, 16:535-539.

Wagner et al., "Antibodies generated from human immunoglobulin miniloci in transgenic mice" (1994) *Nucl. Acids Res.* 22:1389-1393.

Wagner et al., "The diversity of antigen-specific monoclonal antibodies from transgenic mice bearing human immunoglobulin gene miniloci" (1994) *Eur. J. Immunol.*, 24:2672-2681.

Ward, "Binding activities of a repertoire of single immunoglobulin variable domains secreted from *Escherichia coli*" (1989) *Nature*, 341:544-546.

Wedemayer et al., "Structural insights into the evolution of an antibody combining site" (1997) *Science*, 276:1665-1669.

Wiendl et al. (BioDrugs. 2002;16(3):183-200).

Williams et al., "Kinetic analysis by stopped-flow radiationless energy transfer studies: effect of anions on the activity of carboxypeptidase A". Biochemistry. 1986, 25, 94-100.

Winter, "Humanized antibodies" (1993) *Immunol. Today*, 14(6):243-246.

Winter, "Making antibodies by phage display technology" (1994) *Annu. Rev. Immunol.*, 12:433-455.

Wurm, FM, "Production of recombinant protein therapeutics in cultivated mammalian cells", Nature Biotechnology 22(11):1393-1398, 2004.

Yigzaw et al., "Exploitation of the adsorptive properties of depth filters for host cell protein removal during monoclonal antibody purification," Biotechnology Progress, (2006) 22(1):288-296.

Yumioka et al., "Screening of effective column rinse solvent for Protein-A chromatography," Protein Expression and Purification, (2010) 70(2): 218-223.

Zatarain-Rios E and Mannik M, "Charge-charge interactions between articular cartilage and cationic antibodies, antigens, and immune complexes," Arthritis Rheum. Nov. 1987;30(1 1):1265-73.

Zhang et al., "Isolation and characterization of charge variants using cation exchange displacement chromatography," 1218(31): 5079-5086, 2011.

Zou et al., "Dominant expression of a 1.3 Mb human Ig kappa locus replacing mouse light chain production" (1996) *FASEB J.*, 10:1227-1232.

Abbott Laboratories Press Release, "Abbott Laboratories Receives FDA Approval Earlier Than Expected for Humira (adalimumab) for the Treatment of Rheumatoid Arthritis," Dec. 31, 2002, pp. 1-4.

Andersen DC, Goochee CF. The effect of cell-culture conditions on the oligosaccharide structures of secreted glycoproteins. Curr Opin Biotechnol. Oct. 1994;5(5):546-9.

Anonymous, "Sachem Displacement Chromatography," Aug. 29, 2012, Retrieved from the internet: <http://www.displacementchromatography.com>, retrieved on Jul. 30, 2014.

(56) References Cited

OTHER PUBLICATIONS

Averginos, Gab '04 Abstracts—GE Healthcare Life Sciences, "Humira manufacturing: challenges and the path taken", France, Oct. 3-5, 2004, published 2005, pp. 14-16.
Barnes et al., "Stability of Protein Production from Recombinant Mammalian Cells," Biotechnology and Bioengineering, 81:6, Mar. 20, 2003, pp. 631-639.
BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf <http://www.bdbiosciences.com/external_files/Doc_Recon_2.0/ab/others/Phytone_Soytone.pd f>), (last accessed Jan. 8, 2015), 4 pages.
Burteau et al. (in Vitro Cell Dev Biol—Animal, Jul. / Aug. 2003. 39-291-296).
Byun, et al. Archives of Biochemistry and Biophysics, "Transport of anti-IL-6 binding fragments into cartilage and the effects of injury," 532 (2013), pp. 15-22.
Canghai, Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.
Chumsae, Chris et al.: "Arginine modifications by methylglyoxal: discovery in a recombinant monoclonal antibody and contribution to acidic species.", Analytical Chemistry 3 Dec 2013, vol. 85, No. 23, Dec. 3, 2013, pp. 11401-11409.
Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.
Crowell, C.K., et al., Amino acid and manganese supplementation modulates the glycosylation state of erythropoietin in a CHO culture system. Biotechnology and bioengineering, Feb. 15, 3008; 96(3):538-549.
Du et al., "Chromatographic analysis of the acidic and basic species of recombinant monoclonal antibodies" MAbs, (2012) Sep.-Oct.; 4(5):578-85.
Ellison, Jay W. et al., "The Nucleotide Sequence of a Human Immunoglobulin Cγ1 Gene," Nucleic Acids Research, vol. 10, No. 13 (1982), 9 pages.
Feng et al., "Cell Culture Processes for Monoclonal Antibody Production," mAbs, 2:5, 466-477, Sep./Oct. 2010.
Fleisher B., Mechanism of glycosylation in the Golgi apparatus. J Histochem Cytochem, Aug. 1983; 31(8):1033-1040.
Folk et al., "Carboxypeptidase B, Purification and Characterization of the Porcine Enzyme," J. Biological Chem, 1960, 235:2272-2277.
Goochee CF The Oligosaccharides of Glycoproteins: Bioprocess Factors Affecting Oligosaccharide Structure and their Effect on Glycoprotein Properties. Nature Biotechnology Dec. 1991 1346-1355.
Gramer M J et al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.
Gramer, M.J., et al., "Manipulation of Antibody Glycoforms in a High-Yield GS-CHO Process to Meet Comparability Requirements", Biotechnology and Bioengineering, vol. 108, No. 7, Jul. 2011, pp. 1591-1602.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Harlow et al., Eds ("Antibodies: A Laboratory Manual" 1988. Cold Spring Harbor Laboratory Press, Chapter 7, pp. 245, 247,and 253).
Harris, Reed J. et al., "Structural Characterization of a Recombinant CD4-IgG Hybrid Molecule," Eur. J. Biochem. 194:611-620 (1990).
Hills, A.E. et al., Metabolic control of recombinant monoclonal antibody N-glycosylation in GS-NS0 cells, Biotechnology and Bioengineering, Oct. 20, 2001; 75(2):239-251.
Hossler et al., (Glycobiology. 2009; 19 (9): 936-949).

Hossler et al.; "Improvement of mammalian cell culture performance through surfactant enabled concentrated feed media"; Biotechnology Progress; 29(4):1023-1033 (2013).
Humira (adalimumab) prescribing information, Dec. 20, 2002, pp. 1-16.
HyClone™ CDM4CHO Catalog listing (last accessed Nov. 17, 2014).
ICH Topic Q6B "Specifications:Test Procedures and Acceptance Criteria for Biotechnological/Biological Products," Sep. 1999, pp. 1-17.
International Preliminary Report on Patentability for Application No. PCT/US2013/031352 dated Nov. 25, 2014, pp. 1-10.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Search Report and Written Opinion for PCT/US2012/035266, dated Feb. 7, 2013 (corresponds to U.S. Appl. No. 13/547,020), 4 pages.
International Search Report and Written Opinion from PCT/US2013/065749 dated Mar. 18, 2014, 18 pages.
International Search Report and Written Opinion from PCT/US2014/024151 dated Aug. 7, 2014, pp. 1-16.
International Search Report from PCT/US2014/024256 dated Jul. 30, 2014, pp. 1-15.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Kwon et al., (Enzyme Microb Technol. 200; 26: 209-215).
Li, Feng, et al., "Cell Culture Processes for Monoclonal Antibody Production," mAbs 2:5, 466-477 (Sep.-Oct. 2010).
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Martinelle, K. et al., Cells and Culture, Proceedings of the 20th ESACT Meeting v4 819-822, Jun. 17-20, 2007.
McAtee et al., "Isolation of monoclonal antibody charge variants by displacement chromatography," Current Protocols in Protein Science, 14 pages.
Parekh RB N-glycosylation and the production of recombinant glycoproteins vol. 7, Issue 5, p. 117-122, May 1989 Trends in Biotechnology.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.

(56) References Cited

OTHER PUBLICATIONS

Sakai et al.; "Use of nonionic surfactants for effective supply of phosphatidic acid in serum-free culture of Chinese hamster ovary cells"; Journal of Bioscience and Bioengineering; 92(3):256-261 (2001).
Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.
Shen, Amy Y. et al., "Recombinant DNA Technology and Cell Line Development," from "Cell Culture Technology for Pharmaceutical and Cell-Based Therapies," CRC Press, 1995, 15-40.
Sigma Catalog "RPMI1640" (last accessed Jan. 22, 2015), 3 pages.
Sigma MSDS for RMPI1640 (last accessed Jan. 22, 2015), 6 pages.
Sundaram et al., "An innovative approach for the characterization of the isoforms of a monoclonal antibody product," Mabs, 3(6):505-512, 2011.
Sung, Hyun Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.
Tess database "Hyclone" Trademark #76244963. Filing date Apr. 23, 2001. Live mark. Last accessed Jan. 21, 2015.
Tess database "Hyclone" Trademark #85769283. Filing date Sep. 30, 2012. Live mark. Last accessed Jan. 21, 2015.
Tharmalingam et al.; "Pluronic Enhances the Robustness and Reduces the Cell Attachment of Mammalian Cells"; Molecular Biotechnology; 39(2):167-177 (2008).
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.
Worthington Biochemical Corporation, porcine pancreas carboxypeptidase B, one page, Feb. 25, 2012.
United States Food and Drug Administration (FDA) Biological Licensing Application File No. 125057 (Adalimumab) (Dec. 31, 2002) (Last Accessed Mar. 4, 2015 at <http://www.fda.gov/Drugs/DevelopmentApprovalProcess/HowDrugsareDevelopedandApproved/ApprovalApplications/TherapeuticBiologicApplications/ucm080610.htm>), 1 page.
Ahmed, M. U.et al.; N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Awdeh, Z.L., A.R. Williamson, and B.A. Askonas, One cell-one immunoglobulin. Origin of limited heterogeneity of myeloma proteins. Biochem J, 1970. 116(2): p. 241-8.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).

Biastoff, S.; et al.; Colorimetric Activity Measurement of a Recombinant Putrescine N-Methyltransferase from *Datura stramonium*; Planta Med. 2006, 72, 1136.
Chang, T. & Wu, L., Methylglyoxal, oxidative streee, and hypertension, Can. J. Physiol. Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.
Chaplen, F.W.R., Incidence and potentiai implications of the toxic metabolite methyiglyoxai in cell culture: A review, C\I1otechnoloqy 26: 173-183, 1998.
Chaplen, FWR; A dissertation entitled Analysis of Methylglyoxal Metabolism in Mammalian Cell Culture; Univ. of Wisconsin-Madison 1996, 218 pages.
Chelius, D. et al.; Identification and Characterization of Deamidation Sites in the Conserved Regions of Human Immunoglobulin Gamma Antibodies, Anal. Chem. 2005, 77,6004-6011.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009.81(15): p. 6449-57.
Cordoba, A.J., et al., Non-enzymatic hinge region fragmentation of antibodies in solution. Journal of Chromatography B, 2005. 818(2): p. 115-121.
Dai, S.; An Integrated Proteomic Analysis of Major Isoaspartyl-Containing Proteins in the Urine of Wild Type and Protein LIsoaspartate O-Methyltransferase-Deficient Mice; Anal. Chem. 2013, 85, 2423-2430.
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Emery, P. "Adalimumab therapy: Clinical findings and implications for integration into clinical guidelines for rheumatoid arthritis." *Drugs of Today*, 41(3): p. 155-153. (2005).
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/0004 81/WC500050867.pdf; 25 pages.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Goswami et al., "Developments and Challenges for mAb-Based Therapeutics," *Antibodies*, 2:452-500, 2013.
Harding et al., "Class switching in human immunoglobulin transgenic mice" (1995) *Ann. NY Acad. Sci.*, 764:536-547.
Harris, R.J., et al., Identification of multiple sources of charge heterogeneity in a recombinant antibody. Journal of Chromatography B: Biomedical Sciences and Applications, 2001. 752(2): p. 233-245.
Hipkiss, A.; Can the beneficial effects of methionine restriction in rats be explained in part by decreased methylglyoxal generation resulting from suppressed carbohydrate metabolism?; Biogerontology 2012, 13, 633-636.
Huang, L., et al., In Vivo Deamidation Characterization of Monoclonal Antibody by LC/MS/MS. Analytical Chemistry, 2005. 77(5): p. 1432-1439.
International Search Report for Application No. PCT/US2014/026606, Dated Dec. 8, 2014, 8 pages.
International Search Report for Application No. PCT/US2014/026636, Dated Jul. 29, 2014, 5 pages.
Jack, M.; Wright, D.; The Role of Advanced Glycation Endproducts and Glyoxalase I in Diabetic Peripheral Sensory Neuropathy; Trans!. Res. 2012, 159, 355-365.

(56) References Cited

OTHER PUBLICATIONS

Jakubowski, H., Protein N-homocysteinylation: implications for atherosclerosis. Biomedicine & amp; Pharmacotherapy, 2001. 55(8): p. 443-447.
Jefferis, R., Glycosylation of Recombinant Antibody Therapeutics. Biotechnology Progress, 2005.21(1): p. 11-16.
Johnson, K.A., et al., Cation exchange HPLC and mass spectrometry reveal C-terminal amidation of an IgG1 heavy chain. Analytical Biochemistry, 2007. 360(1): p. 75-83.
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Kingkeohoi, S. & Chaplen, F.W.R., Analysis of methylglyoxal metabolism in CHO celis grown in culture, Cytotechnology (2005) 48:1-13.
Leusch, "Failure to demonstrate TNFα-specific autoantibodies in human sera by ELISA and Western blot" (1991) *J. lmmunol. Methods*, 139:145-47.
Liu, H., et al., Heterogeneity of monoclonal antibodies. Journal of Pharmaceutical Sciences, 2008. 97(7): p. 2426-2447.
Liu, H., Gaza-Bulseco, G., & Lundell, E., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Liu, M, et al.; Discovery of Undefined Protein Cross-Linking Chemistry: A Comprehensive Methodology Utilizing 18O- Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Lo, T.W. et al., Binding and modification of proteins by methyiglyoxai under physioiogical conditions. A kinetic and mechanistic study with N alpha-acetylarginine, N-alpha-acetylcysteine, and N alpha-acetyilysine, and bovine serum albumin, Dec. 23, 1994, The Journal of Biological Chemistry, 269, 32299-32305.
Manning, M., et al., *Stability of Protein Pharmaceuticals: An Update*. Pharmaceutical Research, 2010.27(4): p. 544-575.
Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.
Mizuochi, T., et al., Structural and numerical variations of the carbohydrate moiety of immunoglobulin G. J Immunol, 1982. 129(5): p. 2016-20.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Ni, W.; Analysis of Isoaspartic Acid by Selective Proteolysis with Asp-N and Electron Transfer Dissociation Mass Spectrometry; Anal. Chem. 2010, 82,7485-7491.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.
Pacis, et al.: "Effects of cell culture conditions on antibody N-linked glycosylation-what affect high mannose 5 glycoform", Biotechnology and Bioengineering vol. 108, No. 10 Oct. 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.

Parekh, R.B., et al., Association of rheumatoid arthritis and primary osteoarthritis with changes in the glycosylation pattern of total serum IgG. Nature, 1985. 316(6027): p. 452-7.
PCT/US2013/069702 International Search Report & Written Opinion mailed Jan. 31, 2014, 13 pages.
Perkins, M.; et. Al. Determination of the Origin of Charge Heterogeneity in a Murine Monoclonal Antibody; M. Pharm. Res. 2000, 17, 1110-1117.
Quan, C., et al., A study in glycation of a therapeutic recombinant humanized monoclonal antibody: Where it is, how it got there, and how it affects charge-based behavior. Analytical Biochemistry, 2008. 373(2): p. 179-191.
Rabbani, N.; Thornalley, P. J.; Glyoxalase in diabetes, obesity and related disorders; Semin. Cell Dev. Biol. 2011, 22, 309-317.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Roy, B.M., et al., Toxic concentrations of exogenously supplied methy!glyoxal in hybridoma cell culture, Cytotechnology (2004) 46:97-107.
Saxena, R. K. et al.; Microbial production and applications of 1 ,2-propanediol; Indian J. Microbiol. 2010,50,2-11.
The Kennedy Institute of Rheumatology, 1995 Annual Scientific Report, "Anti-TNF trials and studies of mechanisms of action".
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Vasilli, P., Annu. Rev. Immunol. 10:411-452 (1992); and Tracey, K. J. And Cerami, A. Annu. Rev. Med. 45:491-503 (1994).
Vlasak, J. & Ionescu, R., Heterogeneity of *Monoclonal Antibodies Revealed by Charge-Sensitive Methods*. Current Pharmaceutical Biotechnology, 2008. 9(6): p. 468-481.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Williams, A. et al., Ion-Exchange Chromatography, Oct. 1998, Supplement 44, pp. 10-10-1-10-10-30.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yuk, I.H. et al., Controlling Glycation of Recombinant Antibody in Fed Batch Cell Cultures, Nov. 2011 , Biotechnology and Bioengineering, vol. 108, No. 11 pp. 2600-2610.
Zang, T.; et al.; Chemical Methods for the Detection of Protein N-Homocysteinylation via Selective Reactions with Aldehydes; Anal. Chem. 2009, 81, 9065-9071.
Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.

(56) References Cited

OTHER PUBLICATIONS

Babcock, James et al., "Partial Replacement of Chemically Defined Media with Plant-Derived Protein Hydrolysates," *BioPharm International*, vol. 23: Jun. 6, 2010, 6 pages.

Bandyopadhyay S., et al. Physicochemical and functional characterization of a biosimilar adalimumab ZRC-3197, Biosimilars, 2015;5, pp. 1-18.

Brock, Jonathan et al., "Detection and identification of arginine modifications on methylglyoxal-modified ribonuclease by mass spectrometric analysis," Journal of Mass Spectrometry, 2007; 42: 89-100.

Dionex Application Note 125 (Monitoring Protein Deamidation by Cation-Exchange Chromatography. 2009; pp. 1-7).

Drew, Berry et al., "The Effects of Media Formulations on the Biochemical Profile of IgG Expressed in Sp2/0 Cells as Measured by Cation Exchange HPLC," European Society of Animal Cell Technology Meeting Jan. 2007, Poster #1115, 1 page.

Extended European Search Report for Application No. 13877986.3. Dated Aug. 4, 2014, 11 pages.

Fahrner et al., "Industrial purification of pharmaceutical antibodies: development, operation, and validation of chromatography processes" Biotechnology and Genetic Engineering Reviews, 18, 2001, pp. 301-327.

Gagnon, P., "Polishing methods for monoclonal IgG purification" Chapter 17, Taylor & Francis Group, LLC, pp. 491-505, 2007.

Gao et al. "Site-selective modifications of arginine residues in human hemoglobin induced by methylglyoxal." Biochemistry, 2006; pp. 15654-15660.

Grosvenor, Sally, "A New Era in Cell Culture Media Development," *BioPharm International*, Jul. 2012 vol. 25: 7, 7 pages.

International Preliminary Report on Patentability for Application No. PCT/US2013/031365, dated Mar. 3, 2015, 9 pages.

Liu et al. "Recovery and purificaiton process development for monoclonal antibody production" MABS, 2(5), pp. 480-499 (2010).

Mehta, et al. "Purifying therapeutic monoclonal antibodies," Chemical Engineering Progress; May 2008, 104, 5; pp. S14-20.

Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.

Oya, Tomoko et al., "Methylglyoxal Modification of Protein," Journal of Biological Chemistry, 1999, vol. 274: 26, pp. 18492-18502.

Rau "Adalimumab (a fully human anti-tumour necrosis factor alpha monoclonal antibody) in the treatment of active rheumatoid arthritis: the initial results of five trials" Ann Rheum Dis 2002,61 (Suppl II): ii70-ii73.

Roe, S. "Separation Based on Structure" Chapter 4, § 5.2, In, Protein Purification Methods; A Practical Approach, Harries, et al. Sep. 1989, p. 203.

Sargent (pp. 1-3, Internet Archive captured Aug. 28, 2013, www.cellculturedish.com/2012/01/cho-cells-the-top-expressionsystem-of-best-selling-biologic-drugs/).

Scientific Discussion. Retrieved from the Internet: <www.ema.europa.eu/dics/en_GB/document_library/EPAR_Sceintific_Discussion/human/00481/WC500050867.pdf> [retrieved on Jun. 29, 2015], EMEA, 2004, 25 pages.

Shubert et al. "Comparison of ceramic hydroxy- and fluoroapatite versus Protein A/G-based resins in the isiolation of a recombinant human antibody from cell culture supernatant" J. Chromatography A, 114 (2007) 106-113.

Wang, Tina et al., "Exploring Post-translational Arginine Modification Using Chemically Synthesized Methylglyoxal Hydroimidazolones," *J. Am. Chem. Soc.*, 2012, 134, pp. 8958-8967.

\* cited by examiner

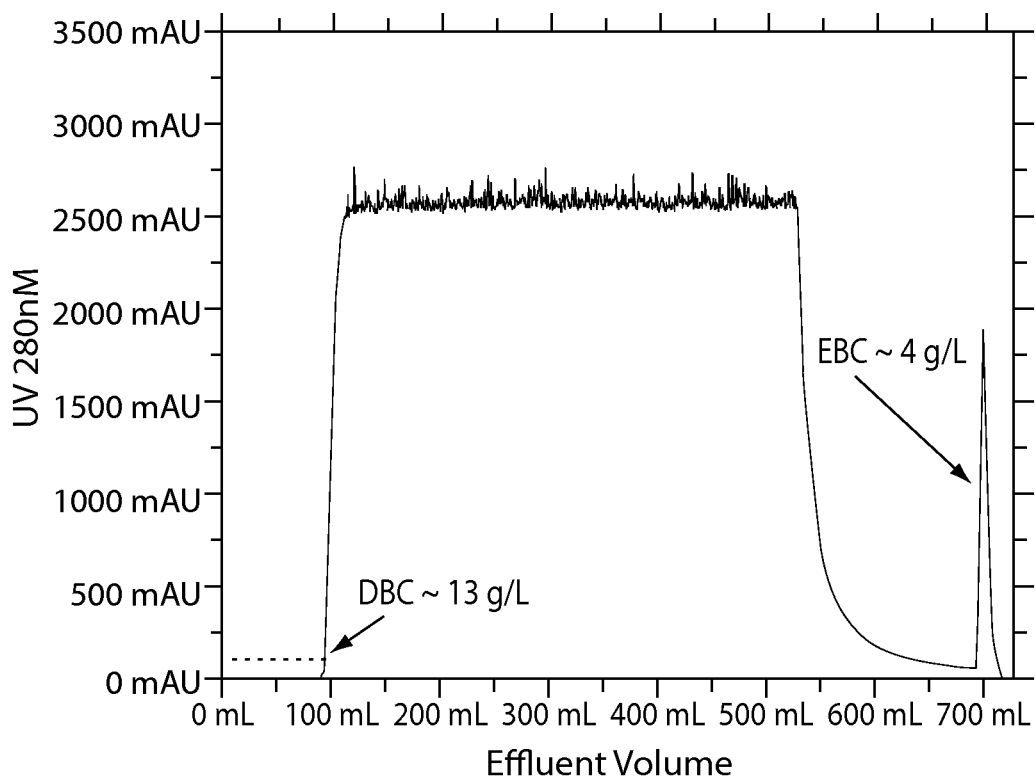

PURIFICATION OF ANTIBODIES USING HYDROPHOBIC INTERACTION CHROMATOGRAPHY

CROSS REFERENCE TO RELATED APPLICATIONS

The present application claims priority to U.S. Provisional Application Nos. 61/651,544, filed on May 24, 2012 and 61/658,920, filed on Jun. 13, 2012, the disclosures of which are incorporated by reference herein in their entireties.

1. INTRODUCTION

The instant invention relates to the field of protein production and purification, and in particular to compositions and processes for controlling the amount of process-related impurities (e.g., host cell proteins and media components) and/or product-related substances (e.g., product charge variants, aggregates, and fragments) present in purified preparations by applying particular chromatography conditions during such protein purification.

2. BACKGROUND OF THE INVENTION

Hydrophobic interaction chromatography (HIC) media interact with hydrophobic regions present on an antibody of interest and the characteristics of that interaction can be calibrated by selecting specific HIC media types and binding conditions. In the context of commercial chromatographic purification, HIC medias are used to separate antibody product present in a variety of sample mixtures, including partially purified samples, e.g., samples that have been subjected to filtration and/or one or more step of affinity, ion exchange, and/or mixed mode chromatography. HIC is conventionally used in such strategies as a means for retaining an antibody product on a chromatographic support, while allowing other components in a partially purified sample, including product-related substances (e.g., product aggregates and fragments) and process-related impurities (e.g., host cell proteins), to be washed from the support and discarded and/or allow for the impurities to be resolved from the antibody product by selective elution of the antibody product. The retained antibody product can then be eluted from the chromatographic support by disrupting the antibody/HIC media interaction and the product can subsequently be subjected to further purification steps, e.g., those relying on charge (e.g., ion exchange chromatography), biological interaction characteristics (e.g., affinity chromatography), and/or size (e.g., ultrafiltration).

There remains a need in the art for high-efficiency methods of purifying antibody products away from product-related substances and process-related impurities at relatively low cost. Reduction of such substances and/or impurities is particularly advantageous in the context of commercially produced recombinant bio-therapeutics as such substances and/or impurities have the potential to impact numerous product characteristics, including, but not limited to, product stability, product safety and product efficacy.

3. SUMMARY OF THE INVENTION

The present invention is directed to compositions and methods for purifying proteins of interest from a sample mixture. In particular, the present invention relates to compositions and methods for purifying proteins employing HIC media. In certain embodiments, the invention provides a method for reducing product-related substances/impurities, including molecular weight variants (e.g., aggregates and fragments of the antibody product), as well as reducing process-related impurities (e.g., host cell proteins). The method involves contacting a sample mixture, e.g., a partially purified cell culture harvest sample, comprising the protein of interest, e.g., and antibody, with a hydrophobic chromatographic media in an aqueous salt solution under loading conditions that permit both the product, i.e., the protein of interest, and non-product proteins to bind to the hydrophobic media and then collecting the unbound product that is substantially reduced in process-related impurities and/or product-related substances from the media. The method further comprises a step whereby the bound product, is subsequently recovered by employing a wash with a similar aqueous salt composition that is present in the load sample while the product-related and process-related impurities remain bound to the HIC media. The wash fraction collected is also substantially reduced in process-related impurities and/or product-related substances In certain embodiments, the purification strategies of the present invention may include one or more chromatography and/or filtration steps to achieve a desired degree of purification prior to exposure of the sample comprising the protein of interest of interest to the HIC media. For example, in certain embodiments, such pre-HIC chromatography step(s) can include one or more step of ion exchange chromatography and/or affinity chromatography. In certain embodiments, the purification strategies of the present invention may include one or more additional chromatography and/or filtration steps after the HIC purification step. In one aspect the filtration step is a nanofiltration step. In addition, in certain embodiments, the present invention is directed toward pharmaceutical compositions comprising one or more proteins of interest purified by methods described herein.

In certain embodiments, the sample mixture (also referred to as the "source material' or simply "sample") comprises a cell culture harvest wherein the cell line is employed to produce specific antibodies of the present invention. In certain embodiments, the sample exposed to the HIC media comprises a cell culture harvest that has undergone one or more purification and/or filtration steps, including but not limited to, one or more step of ion exchange chromatography and/or affinity chromatography.

In certain embodiments, an affinity chromatography step will precede the HIC chromatography step, thereby forming an affinity chromatography sample that can be exposed to the HIC media in the HIC chromatography step. In certain embodiments, the affinity chromatography step is a Protein A, G, A/G, or L affinity chromatography step. There are several commercial sources for Protein A media. One suitable media is MabSelect™ from GE Healthcare. In certain embodiments, the affinity chromatography sample is further subject to a filtration step. Filters well known to those skilled in the art can be used in this embodiment. In one aspect, the filtration step is a depth filtration step.

In certain embodiments, an affinity chromatography step will follow, directly or indirectly, the HIC chromatography step, thereby forming an affinity chromatography sample. In certain embodiments, the affinity chromatography step is a Protein A, G, A/G, or L affinity chromatography step. There are several commercial sources for Protein A media. One suitable media is MabSelect™ from GE Healthcare. In certain embodiments, the affinity chromatography sample is further subject to a filtration step. Filters well known to those skilled in the art can be used in this embodiment. In one aspect, the filtration step is a nanofiltration step.

In certain embodiments, an ion exchange step will precede the HIC chromatography step, thereby forming an ion exchange sample that can be exposed to the HIC media in the HIC chromatography step. In certain embodiments, the ion exchange step is either a cation exchange step or an anion exchange step. In certain embodiments, the ion exchange step is a single ion exchange chromatographic step or can include multiple ion exchange steps such as a cation exchange step followed by an anion exchange step or visa versa. In one aspect, the ion exchange step is a one step procedure. In certain embodiments, the ion exchange step involves a two step ion exchange process. A suitable cation exchange media is a media whose stationary phase comprises anionic groups. Examples of such a cation exchange media include, but are not limited to Fractogel, carboxymethyl (CM), sulfoethyl (SE), sulfopropyl (SP), phosphate (P) and sulfonate (S). In certain embodiments, the cation exchange media is Fractogel™ $SO_3^-$. This ion exchange capture chromatography step facilitates the isolation of proteins of interest, e.g., antibodies, from a sample. A suitable anion exchange media is a media whose stationary phase comprises cationic groups. Examples of such an anion exchange media include, but are not limited to, Q sepharose, diethylaminoethyl (DEAF), quaternary aminoethyl (QAE), and quaternary amine (Q) groups. In certain embodiments, the anion exchange media is Q Sepharose™. One or more ion exchange step further isolates antibodies by reducing process-related impurities such as host cell proteins and DNA and, where applicable, affinity matrix protein. In certain embodiments, an ion exchange sample is further subject to a filtration step. Filters well known to those skilled in the art can be used in this embodiment. In one aspect, the filtration step is a depth filtration step. In certain embodiments, a filtration step follows the depth filtration step.

In certain embodiments, an ion exchange step will follow, directly or indirectly, the HIC chromatography step, thereby forming an ion exchange sample. In certain of such embodiments, the ion exchange step is either a cation exchange step or an anion exchange step. In certain embodiments, the ion exchange step is a single ion exchange chromatographic step or can include multiple ion exchange steps such as a cation exchange step followed by an anion exchange step or visa versa. In one aspect, the ion exchange step is a one step procedure. In certain embodiments, the ion exchange step involves a two step ion exchange process. A suitable cation exchange media is a media whose stationary phase comprises anionic groups. Examples of such a cation exchange media include, but are not limited to Fractogel, carboxymethyl (CM), sulfoethyl (SE), sulfopropyl (SP), phosphate (P) and sulfonate (S). In certain embodiments, the cation exchange media is Fractogel™ $SO_3^-$. This ion exchange capture chromatography step facilitates the isolation of antibodies from a sample. A suitable anion exchange media is a media whose stationary phase comprises cationic groups. Examples of such an anion exchange media include, but are not limited to, Q sepharose, diethylaminoethyl (DEAE), quaternary aminoethyl (QAE), and quaternary amine (Q) groups. In certain embodiments, the anion exchange media is Q Sepharose™. In certain embodiments, an ion exchange sample is further subject to a filtration step. Filters well known to those skilled in the art can be used in this embodiment.

In certain embodiments, a mixed mode chromatography step will precede the HIC chromatography step, thereby forming a mixed mode chromatography sample that can be exposed to the HIC media in the HIC chromatography step. Examples of mixed mode medias include, but are not limited to: CaptoAdhere (GE Healthcare), PPA-HyperCel (Pall Life Sciences), and HEA-HyperCel (Pall Life Sciences). In certain embodiments, the mixed mode chromatography step is a CaptoAdhere chromatography step. In certain embodiments, the mixed mode chromatography sample is further subject to a filtration step. Filters well known to those skilled in the art can be used in this embodiment. In certain embodiments, a depth filtration step follows a filtration step.

In certain embodiments, a mixed mode chromatography step will follow, directly or indirectly, the HIC chromatography step, thereby forming a mixed mode chromatography sample. Examples of mixed mode medias include, but are not limited to: CaptoAdhere (GE Healthcare), PPA-HyperCel (Pall Life Sciences), and HEA-HyperCel (Pall Life Sciences). In certain embodiments, the mixed mode chromatography step is a CaptoAdhere chromatography step. In certain embodiments, the mixed mode chromatography sample is further subject to a filtration step. Filters well known to those skilled in the art can be used in this embodiment. In one aspect, the filtration step is a nanofiltration step. In certain embodiments, a depth filtration step follows a filtration step.

In certain embodiments, the present invention is directed toward methods of purifying a protein of interest, e.g., an antibody, from a sample mixture such that the resulting composition is substantially free of host cell proteins ("HCPs"). In addition, the purity of the proteins of interest in the resultant sample can be analyzed using methods well known to those skilled in the art, e.g., size-exclusion chromatography, Protein A HPLC Assay, HCP ELISA, Protein A ELISA, and western blot analysis.

In certain embodiments, the protein of interest is an antibody, such as, but not limited to a human antibody, a humanized antibody, a chimeric antibody, or a multivalent antibody, such as a DVD-Ig.

In certain embodiments, the invention is directed to one or more pharmaceutical compositions comprising an isolated protein of interest, e.g., an antibody, in the context of a process-related impurity-reduced and/or product-related substance-reduced preparation and an acceptable carrier. In certain embodiments, the compositions further comprise one or more pharmaceutical agents.

4. BRIEF DESCRIPTIONS OF THE DRAWINGS

FIG. 1 depicts a process chromatogram for the HIC purification of Adalimumab, wherein a GE CaptoPhenyl column was equilibrated at 1.1 M $AmSO_4$ pH 7.0 (Tris/Acetate) for 10 CVs, Adalimumab was prepared at 1.1 M $AmSO_4$ and loaded to the column at 20 g-protein/L of media, the column was then washed with 10 CVs of the equilibration buffer and a linear gradient from 1.1M to 0M $AmSO_4$ pH 7.0 (Tris/Acetate) over 20 CVs was performed.

FIG. 2 depicts a process chromatogram for the HIC purification of Adalimumab, wherein a GE CaptoPhenyl column was equilibrated with 400 mM NaCit pH 5.6 for 10 CVs, Adalimumab was prepared at 400 mM NaCit pH 5.6, then loaded to the column at 500 g-protein/L-media, and the column was washed with 7 CVs of the equilibration buffer.

FIG. 4 depicts an example of hybrid chromatography mode (i.e., a chromatographic mode having characteristics of both batch-elute and flow-through chromatography) wherein, based on the data presented in FIG. 2, the dynamic binding capacity (DBC), conventionally measured at 10% breakthrough, is greater than the equilibrium binding capacity (EBC).

Figure 5A:
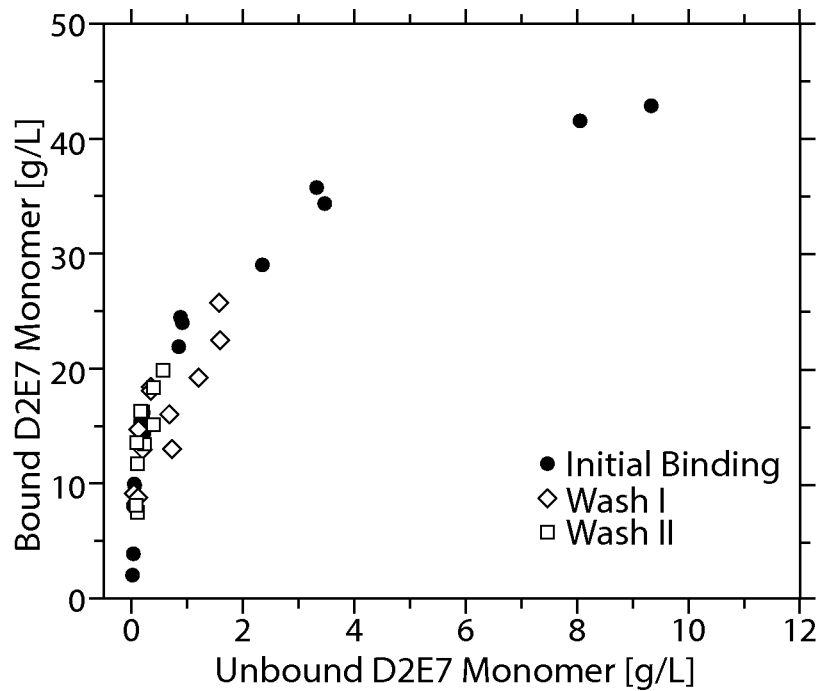
Figure 5B:
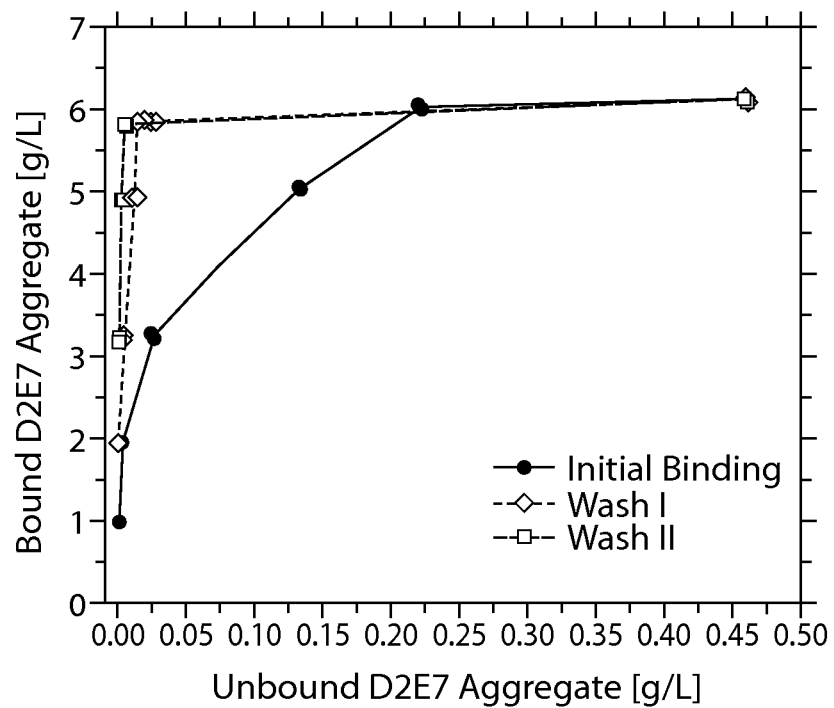

FIG. 5A-B depict the results of experiments wherein aliquots of resin are incubated with a load covering a range of protein concentrations at room temperature for 3 hours, after which the protein solution is then removed, and replaced with equilibration buffer (Wash simulation) and incubated at room temperature for 3 hours (repeated, Wash II). After each incubation, the concentration of the protein solution is measured and used to calculated the amount of protein ((A) monomer D2E7, a.ka. Adalimumab, and (B) aggregate D2E7) bound to the resin (g protein/L resin) and plotted against the concentration of the protein solution at the end of the incubation (e.g. equilibrium).

Figure 6A:
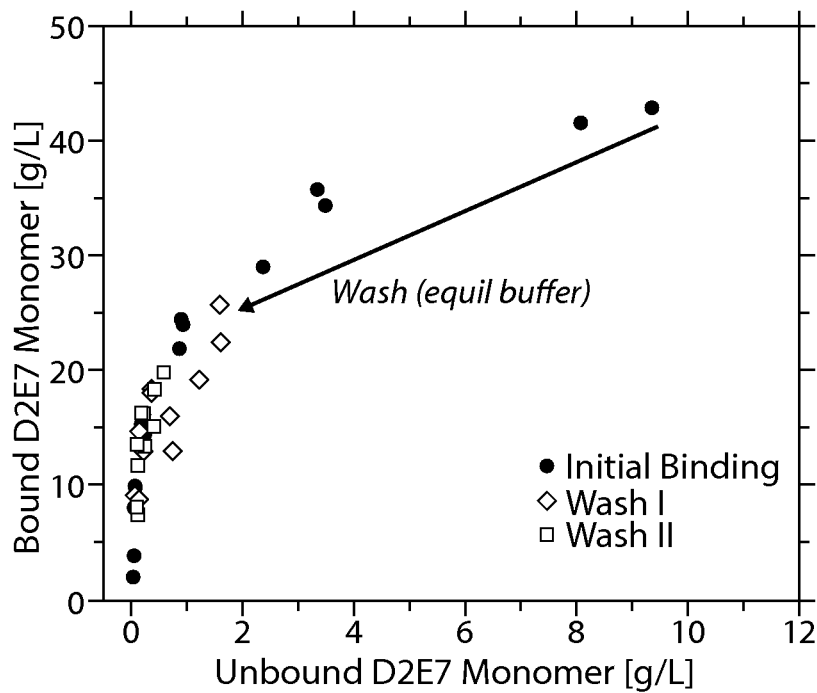
Figure 6B:
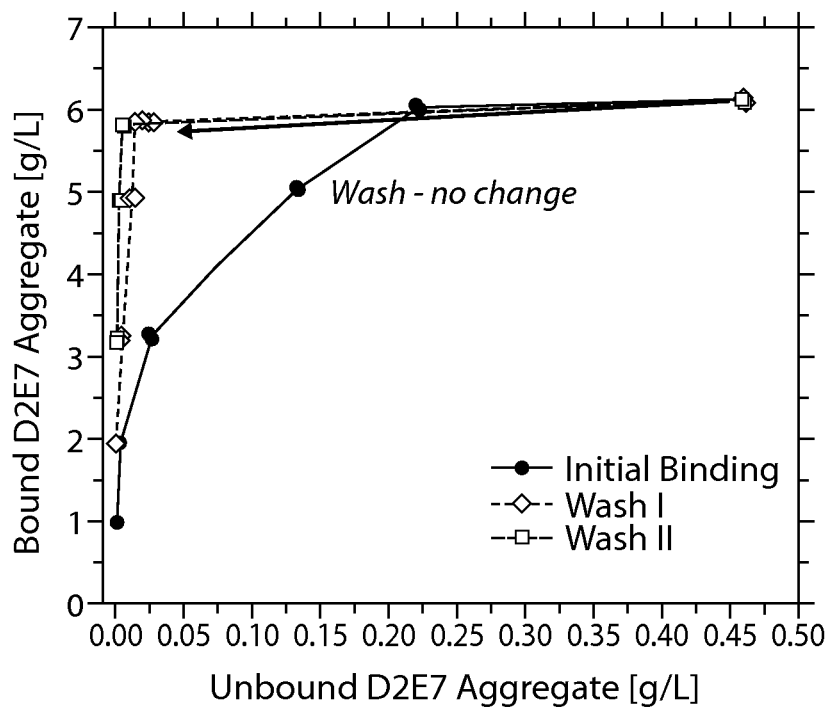

FIG. 6A-B depict the results outlined in FIGS. 5A-B, highlighting the fact that at initial equilibrium a significant amount of monomer/aggregate is bound to the resin. However, after the protein solution is replaced with equilibration buffer (see arrow), the monomer de-sorbs from the resin and back into solution, where as the aggregate remains bound.

Figure 7A:
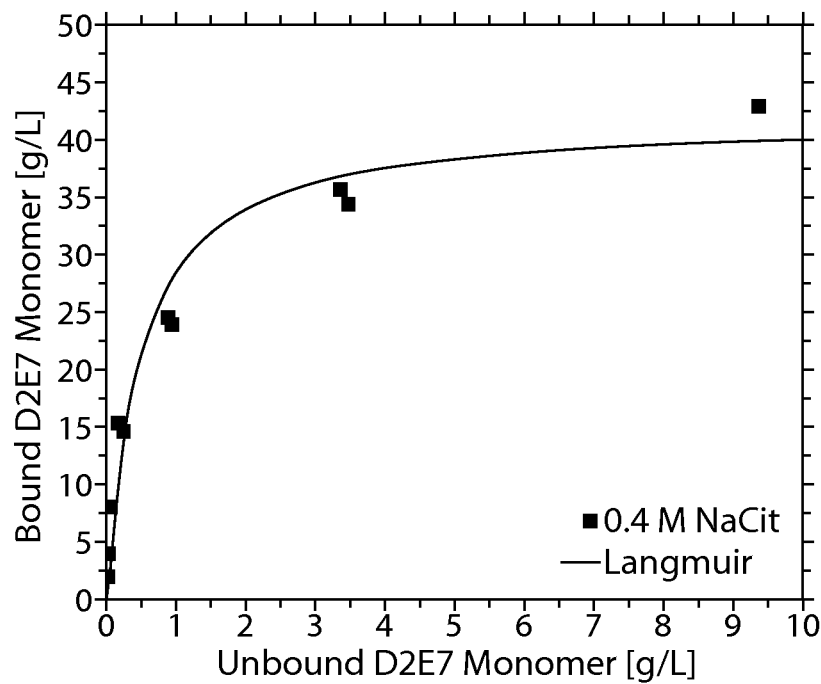
Figure 7B:
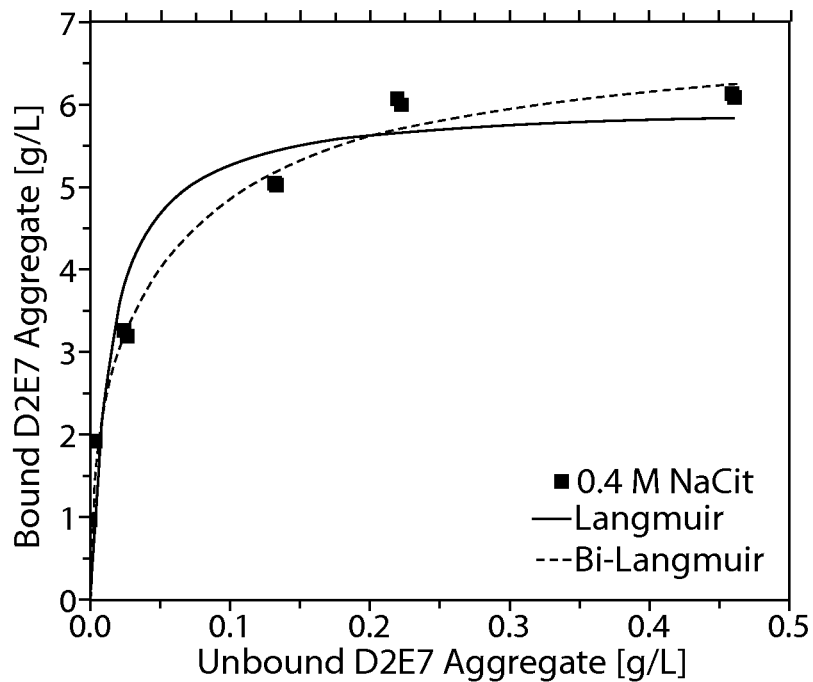

FIG. 7A-B depict a determination of the binding monomer and aggregate D2E7 (based on data provided in FIGS. 5A-B) by fitting the experimental equilibrium binding data to the Langmuir Isotherm using the equation: $q=(q_{max} \times C_{eqil})/(K_d + C_{equil})$; where q=amount of protein bound to resin [=] g/L-resin; $q_{max}$=maximum amount of protein bound to resin [=] g/L-resin; $C_{equil}$=solution concentration of protein [=] g/L-soln; and $K_d$=equilibrium dissociation constant.

5. DETAILED DESCRIPTION OF THE INVENTION

The present invention is directed to compositions and methods for purifying antibody products from a sample matrix. In particular, the present invention relates to compositions and methods for purifying antibody products employing HIC media. In certain embodiments, the invention provides a method for modulating the content of product-related substances, including molecular weight variants (e.g., aggregates and fragments of the antibody product), in a purified sample of a protein of interest as well as reducing process-related impurities (e.g., host cell proteins). The method involves contacting a sample mixture, e.g., a partially purified cell culture harvest sample, comprising the protein of interest, e.g., and antibody, with a hydrophobic chromatographic media in an aqueous salt solution under loading conditions that permit both the product, i.e., the protein of interest, and non-product proteins to bind to the hydrophobic media and then collecting the unbound product that is substantially reduced in process-related impurities and/or product-related substances from the media. The method further comprises a step whereby the bound product, is subsequently recovered by employing a wash with a similar aqueous salt composition that is present in the load sample while the product-related and process-related impurities remain bound to the HIC media. The wash fraction collected is also substantially reduced in process-related impurities and/or product-related substances In certain embodiments, the purification strategies of the present invention may include one or more chromatography and/or filtration steps to achieve a desired degree of purification prior to exposure of the sample comprising the antibody of interest to the HIC media. For example, in certain embodiments, such pre-HIC chromatography step(s) can include one or more step of ion exchange chromatography and/or affinity chromatography. In certain embodiments, the purification strategies of the present invention may include one or more additional chromatography and/or filtration steps after the HIC purification step. In addition, in certain embodiments, the present invention is directed toward pharmaceutical compositions comprising one or more antibodies purified by methods described herein.

For clarity and not by way of limitation, this detailed description is divided into the following sub-portions:
   5.1. Definitions;
   5.2. Antibody Generation;
   5.3. Antibody Production;
   5.4. Antibody Purification;
   5.5. Methods of Assaying Sample Purity;
   5.6. Further Modifications; and
   5.7. Pharmaceutical Compositions

5.1. Definitions

In order that the present invention may be more readily understood, certain terms are first defined.

The term "product", as used herein refers to a protein of interest, which may be present in the context of a sample comprising one or more process-related impurities and/or product-related substances. In certain embodiments, the product, i.e., the protein of interest, is an antibody or antigen binding fragment thereof.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody", as used herein, also includes alternative antibody and antibody-like structures, such as, but not limited to, dual variable domain antibodies (DVD-Ig).

The term "antigen-binding portion" of an antibody (or "antibody portion") includes fragments of an antibody that retain the ability to specifically bind to an antigen (e.g., hIL-12, hTNFα, or hIL-18). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody may be part of a larger immunoadhesion molecule, formed by covalent or non-covalent association of the antibody with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The terms "Kabat numbering" "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242, the entire teachings of which are incorporated herein by reference). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities. Moreover, an isolated antibody may be substantially free of other cellular material and/or chemicals.

The term "Koff", as used herein, is intended to refer to the off rate constant for dissociation of an antibody from the antibody/antigen complex.

The term "Kd", as used herein, is intended to refer to the dissociation constant of a particular antibody-antigen interaction.

The phrase "nucleic acid molecule" includes DNA molecules and RNA molecules. A nucleic acid molecule may be single-stranded or double-stranded, but in one aspect is double-stranded DNA.

The phrase "isolated nucleic acid molecule," as used herein in reference to nucleic acids encoding antibodies or antibody portions (e.g., VH, VL, CDR3), e.g. an antibody having a weak binding capacity for a Protein A media (e.g., a canine monoclonal antibody 82.4). The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "host cell proteins" (HCPs), as used herein, is intended to refer to non-target protein-related, proteinaceous impurities derived from host cells.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "preparative scale", as used herein, refers to a scale of purification operation that can be readily scaled-up and implemented at large scale manufacturing while still providing desired separation. For instance, one skilled in the field may develop a process using, e.g., a 0.5 cm (i.d.)×20 cm (length) column in the lab, and transfer it to large scale production using, e.g., a 30 cm (i.d.)×20 cm (length) column packed with the same media and operated with the same set of buffers, same linear flow rates (or residence times) and buffer volumes. In preparative scale separation, column bed height is typically ≤about 30 cm and column pressure drop ≤about 5 bar.

The term "aggregates" used herein means agglomeration or oligomerization of two or more individual molecules, including but not limiting to, protein dimers, trimers, tetramers, oligomers and other high molecular weight species. Protein aggregates can be soluble or insoluble.

The term "fragments" used herein refers to any truncated protein species from the target molecule due to dissociation of peptide chain, enzymatic and/or chemical modifications. For instance, antibody fragments include, but not limited to, Fab, F(ab')$_2$, Fv, scFv, Fd, dAb, or other compositions that contain a portion of the antibody molecule.

The term "charge variants", as used herein, refers to the full complement of product variants including, but not limited to acidic species, and basic species (e.g., Lys variants). In certain embodiments, such variants can include product aggregates and/or product fragments, to the extent that such aggregation and/or fragmentation results in a product charge variation as seen in an analytical technique used for that purpose.

As used herein, the term "lysine variant heterogeneity" refers to a characteristic of a population of proteins wherein the population consists of proteins of substantially identical amino acid sequence, but where the population exhibits variation in the presence or absence of C-terminal lysine residues.

In certain embodiments, the protein is an antibody, and the distribution of lysine variant heterogeneity comprises a distribution of the lysine variants Lys 0, Lys 1 and Lys 2, wherein the Lys 0 lysine variant comprises an antibody with heavy chains that do not comprise a C-terminal lysine, wherein the Lys 1 lysine variant comprises an antibody with one heavy chain that comprises a C-terminal lysine, and wherein the Lys 2 lysine variant comprises an antibody wherein both heavy chains comprise a C-terminal lysine.

In certain embodiments, C-terminal lysine variants are associated with charge heterogeneities present in protein preparations, for example, monoclonal antibody (mAb) preparations, produced through a cell culture process. These heterogeneities can be detected by various methods, such as, for example, WCX-10 HPLC (a weak cation exchange chromatography), or IEF (isoelectric focusing).

In certain embodiments, the heterogeneity arises from subspecies of protein differing by the presence or absence of C-terminal lysines. For example, the population of proteins may comprise more than one subspecies of lysine variant. In one non-limiting example, the lysine variants may comprise at least two of Lys 0, Lys 1 and Lys 2 lysine variants which can be detected by weak cation exchange chromatography of the expression product of a host cell expressing Adalimumab.

In certain embodiments, the heterogeneity arises from the size of subpopulations having different C-terminal lysine profiles. For example, the population of proteins may comprise more than one subspecies of C-terminal lysine variant, and each of the variants may be present in different amounts. In one non-limiting example, the C-terminal lysine variants may be at least two of the Lys 0, Lys 1 and Lys 2 lysine variants detected by weak cation exchange chromatography of the expression product of a host cell expressing Adalimumab. In certain embodiments, Lys 0, Lys 1 or Lys 2 subspecies are present in different amounts.

In certain embodiments, the heterogeneity arises from both a difference in the amount of lysine variants in the population of proteins and the type of lysine variants present in the population of proteins.

As used herein, the terms "acidic species", "acidic region" and "acidic species heterogeneity" refer to a characteristic of a population of proteins wherein the population includes a distribution of product-related substances identifiable by the presence of charge heterogeneities. For example, in monoclonal antibody (mAb) preparations, such acidic species heterogeneities can be detected by various methods, such as, for example, WCX-10 HPLC (a weak cation exchange chromatography), or IEF (isoelectric focusing). In certain embodiments, the acidic species identified using such techniques comprise a mixture of product-related substances containing antibody product fragments (e.g., Fc and Fab fragments), aggregates, and/or post-translation modifications of the antibody product, such as, deamidated and/or glycoslyated antibodies.

In certain embodiments, the acidic species heterogeneity comprises a difference in the type of acidic species present in the population of proteins. For example, the population of proteins may comprise more than one acidic species variant.

In certain embodiments, the heterogeneity of the distribution of acidic species comprises a difference in the amount of acidic species in the population of proteins. For example, the population of proteins may comprise more than one acidic species variant, and each of the variants may be present in different amounts.

5.2. Antibody Generation

The term "antibody" as used in this section refers to an intact antibody or an antigen binding fragment thereof.

The antibodies of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

In certain embodiments, the animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody can be, in certain embodiments, a human, a chimeric, or a humanized antibody. Humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

Human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen).

Moreover, alternative transchromosomic animal systems expressing human immunoglobulin genes are available in the art and can be used to raise antibodies of the disclosure. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise the antibodies of this disclosure.

In certain embodiments, the antibodies of this disclosure are recombinant human antibodies, which can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226: 889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The antibodies or antigen-binding portions thereof, of this disclosure can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

5.3. Antibody Production

To express an antibody of the invention, DNAs encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr– host cells with methotrexate selection/amplification) and the neo gene (for G418 selection).

An antibody of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant antibodies of the invention include Chinese Hamster Ovary (CHO cells) (including dhfr– CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23; 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as Ham's F10™ (Sigma), Minimal Essential Medium™ ((MEM), (Sigma), RPMI-1640 (Sigma), and Dulbecco's Modified Eagle's Medium™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to the antigen to which the putative antibody of interest binds. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the one to which the putative antibody of interest binds, depending on the specificity of the antibody of the invention, by crosslinking an antibody of the invention to a second antibody by standard chemical crosslinking methods.

In a suitable system for recombinant expression of an antibody of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space, or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of antibodies from cell debris initially depend on the site of expression of the antibody. Some antibodies can be secreted directly from the cell into the surrounding growth media; others are made intracellularly. For the latter antibodies, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

5.4. Antibody Purification

5.4.1 Antibody Purification Generally

In certain embodiments, the invention provides methods and compositions for producing a purified or partially purified (e.g., process-related impurity-reduced and/or product-related substance-reduced) protein preparation from a mixture comprising a protein of interest, e.g., an antibody, and at least one process-related impurity or product-related substance. In certain embodiments, the compositions of the present invention include, but are not limited to, process-related impurity-reduced and/or product-related substance-reduced compositions comprising a protein of interest. For example, but not by way of limitation, the present invention is directed to process-related impurity-reduced and/or product-related substance-reduced compositions comprising Adalimumab. Such process-related impurity-reduced and/or product-related substance-reduced compositions process-related impurity-reduced and/or product-related substance-reduced compositions address the need for improved product characteristics, including, but not limited to, product stability, product safety and product efficacy.

In certain embodiments, the present invention is directed to a method for preparing a process-related impurity-reduced and/or product-related substance-reduced composition comprising a protein of interest wherein a chromatographic separation is performed to identify the particular conditions, e.g., salt concentration, pH, temperature, load amount and conditions, and washing conditions, sufficient to elicit the desired fractionation profile of a sample comprising the protein of interest and at least one process-related impurity and/or at least one product-related substance. In certain embodiments, the method will further comprise pooling of the resulting fractions comprising the desired process-related impurity-reduced and/or product-related substance-reduced composition comprising a protein of interest.

In certain embodiments, the purification process of the invention begins at the separation step when the antibody has been produced using production methods described above and/or by alternative production methods conventional in the art. Once a clarified solution or mixture comprising the antibody has been obtained, separation of the protein of interest from process-related impurities, such as the other proteins produced by the cell, as well as any product-related substances such as charge variants and/or size variants (aggregates and fragments), can be performed using a HIC separation step, or a combination of a HIC separation step and one or more purification techniques, including filtration and/or affinity, ion exchange, and/or mixed mode chromatographic step(s), as outlined herein. The essence of each of the chromatographic separation methods is that proteins can be caused either to traverse at different rates down a column, achieving a physical separation that increases as they pass further down the column, or to adhere selectively to the separation medium, being then differentially eluted by different solvents. In some cases, the protein of interest is separated from impurities and or product-related substances when the impurities and/or product-related substances specifically adhere to the column and the protein of interest does not, i.e., the protein of interest is washed from the column, while in other cases the protein of interest will adhere to the column, while the impurities and/or product-related substances are washed from the column.

5.4.2 Primary Recovery

In certain embodiments, the initial steps of the purification methods of the present invention involve the clarification and primary recovery of antibody from a sample matrix. In certain embodiments, the primary recovery will include one or more centrifugation steps to separate the antibody product from the cells and cell debris. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification, or in-line filtered through one or more depth filters for further clarification of the sample.

In certain embodiments, the primary recovery will include the use of one or more depth filtration steps to clarify the sample matrix and thereby aid in purifying the antibodies of interest in the present invention. In other embodiments, the primary recovery will include the use of one or more depth filtration steps post centrifugation to further clarify the sample matrix. Non-limiting examples of depth filters that can be used in the context of the instant invention include the Millistak+X0HC, F0HC, D0HC, A1HC, B1HC depth filters (EMD Millipore), Cuno™ model 30/60ZA, 60/90 ZA, VR05, VR07, delipid depth filters (3M Corp.). A 0.2 μm filter such as Sartorius's 0.45/0.2 μm Sartopore™ bi-layer or Millipore's Express SHR or SHC filter cartridges typically follows the depth filters.

In certain embodiments, the primary recovery process can also be a point at which to reduce or inactivate viruses that can be present in the sample matrix. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972. In certain embodiments of the present invention, the sample matrix is exposed to detergent viral inactivation during the primary recovery phase. In other embodiments, the sample matrix may be exposed to low pH inactivation during the primary recovery phase.

In those embodiments where viral reduction/inactivation is employed, the sample mixture can be adjusted, as needed, for further purification steps. For example, following low pH viral inactivation, the pH of the sample mixture is typically adjusted to a more neutral pH, e.g., from about 4.5 to about 8.5, prior to continuing the purification process. Additionally, the mixture may be diluted with water for injection (WFI) to obtain a desired conductivity.

5.4.3 Hydrophobic Interaction Chromatography

In certain embodiments, the instant invention features methods for producing a process-related impurity and/or product-related substance-reduced protein preparation from a mixture comprising a protein of interest, e.g., an antibody, and at least one process-related impurity and/or product-related substance comprising a hydrophobic interaction chromatography (HIC) step.

In performing the HIC separation, the sample mixture is contacted with the HIC material, e.g., using a batch purification technique or using a column or membrane chromatography or monolithic material (referred to as HIC media). Prior to HIC purification it may be desirable to adjust the concentration of the salt concentration in the buffer to achieve desired protein binding to the HIC media.

For example, in the context of batch purification, HIC material is prepared in or equilibrated with a desired equilibration buffer. A slurry of the HIC material is obtained. The protein solution is contacted with the slurry to allow protein adsorption to the HIC material. The solution comprising the process-related impurities and/or product-related substances that do not bind to the HIC material is separated from the slurry, e.g., by allowing the slurry to settle and removing the supernatant. The slurry can be subjected to one or more washing steps and/or elution steps.

In the context of chromatographic separation, a chromatographic apparatus, commonly cylindrical in shape, is employed to contain the chromatographic support material (e.g., HIC material) prepared in an appropriate buffer solution. The chromatographic apparatus, if cylindrical, can have a diameter of about 5 mm to about 2 meters, and a height of 5 cm to 50 cm, and in certain embodiments, particularly for large scale processing, a height of ≤30 cm is employed. Once the chromatographic material is added to the chromatographic apparatus, a sample containing the protein of interest, e.g., an antibody, is contacted to the chromatographic material to induce the separation. Any portion of the solution that does not bind to the chromatographic material, e.g., which may comprise, depending on the HIC material being employed, the protein of interest, process-related impurities, and/or product-related substances, is separated from the chromatographic material by washing the material and collecting fractions from column. The chromatographic material can be subjected to one or more wash steps. If desired, the chromatographic material can then be contacted with a solution of designed to desorb any components of the solution that have bound to the chromatographic material.

Hydrophobic interaction chromatography employs the hydrophobic properties of proteins to achieve separation of even closely-related molecules. Hydrophobic groups on the protein interact with hydrophobic groups of the media or the membrane. In certain embodiments, the more hydrophobic a protein is the stronger it will interact with the column or the membrane. Thus, HIC steps, such as those disclosed herein, can be used to remove a variety of process-related impurities (e.g., DNA) as well as product-related species (e.g., high and low molecular weight product-related species, such as protein aggregates and fragments).

An HIC column or membrane device can be operated in a bind-elute mode, a flow-through mode, or a hybrid mode wherein the product exhibits binding to the chromatographic material, yet can be washed from the column using a buffer that is the same or substantially similar to the loading buffer. The bind-elute mode of operation has been explained above in connection with batch purification. For flow-through, process-related impurities, such as HCPs, and product-related substances, such as aggregates, will, in certain embodiments, depending the particular HIC material employed, bind to the HIC media while product flows through the column. A hybrid mode, in contrast, can involve the use of an HIC media that allows for the product to be immobilized on the chromatographic support in the presence of a loading buffer, but then removed by successive washes of buffer identical to or substantially similar, for example, but not by way of limitation where the salt concentration is adjusted within about 20% of the concentration of the loading buffer. In certain embodiments, a step-wise or linear change in wash conductivity can be used. In the context of this hybrid strategy, process-related impurities and product-relates substances will either bind to the chromatographic material or flow through with a profile distinct from the protein of interest. After loading, the column can be regenerated with water and cleaned with caustic solution to remove the bound impurities before next use.

Hydrophobic interactions are strongest at high salt concentration (and hence the ionic strength of the anion and cation components), therefore, this form of separation is conventionally performed following salt elution step, e.g., the type of elution step typically used in connection with ion exchange chromatography. Adsorption of the antibody to a HIC column is favored by high salt concentrations, but the actual concentrations can vary over a wide range depending on the nature of the protein of interest, salt type and the particular HIC ligand chosen. For example, and not by way of limitation, the salt concentrations shown to be effective in aggregate reduction are in the range of 80 mM-1000 mM, depending on the salt type and HIC adsorbent. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{2+}$; $Ca^{2+}$; $Mg^{2+}$; $Li^+$; $Cs^+$; $Na^+$; $K^+$; $Rb^+$; $NH_4^+$, while anions may be ranked in terms of increasing chaotropic effect as $PO_4^{3-}$; $SO_4^{2-}$; $CH3CO_3^-$; $Cl^-$; $Br^-$; $NO_3^-$; $ClO_4^-$; $I^-$; $SCN^-$.

In certain embodiments, the anionic part of the salt is chosen from among sulfate, citrate, chloride, or a mixture thereof. In certain embodiments, the cationic part of the salt is chosen from among ammonium, sodium, potassium, or a mixture thereof. In general, $Na^+$, $K^+$ or $NH_4^+$ sulfates effectively promote ligand-protein interaction in HIC. Salts may be formulated that influence the strength of the interaction as given by the following relationship: $(NH_4)_2SO_4 > Na_2SO_4 > NaCl > NH_4Cl > NaBr > NaSCN$. In general, salt concentrations of between about 0.75 and about 2 M ammonium sulfate or between about 1 and 4 M NaCl are useful.

In certain embodiments, the HIC adsorbent material is composed of a chromatographic backbone with pendant hydrophobic interaction ligands. For example, by not by way of limitation, the HIC adsorbent material can be composed of convective membrane media with pendent hydrophobic interaction ligands, convective monolithic media with pendent hydrophobic interaction ligands, and/or convective filter media with embedded media containing the pendant hydrophobic interaction ligands. In certain embodiments, the HIC adsorbent material can comprise a base matrix (e.g., cross-linked agarose or synthetic copolymer material) to which hydrophobic ligands (e.g., alkyl or aryl groups) are coupled. One, non-limiting, example of a suitable HIC media comprises an agarose media or a membrane functionalized with phenyl groups (e.g., a Phenyl Sepharose™ from GE Healthcare or a Phenyl Membrane from Sartorius). Many HIC medias are available commercially. Examples include, but are not limited to, Capto Phenyl, Phenyl Sepharose™ 6 Fast Flow with low or high substitution, Phenyl Sepharose™ High Performance, Octyl Sepharose™ High Performance (GE Healthcare); Fractogel™ EMD Propyl or Fractogel™ EMD Phenyl (E. Merck, Germany); Macro-Prep™ Methyl or Macro-Prep™ t-Butyl columns (BioRad, California); WP HI-Propyl (C3)™ (J. T. Baker, New Jersey); Toyopearl™ ether, phenyl or butyl (TosoHaas, PA); ToyoScreen PPG, ToyoScreen Phenyl, ToyoScreen Butyl, and ToyoScreen Hexyl are a rigid methacrylic polymer bead. GE HiScreen Butyl FF and HiScreen Octyl FF are high flow agarose based beads.

In certain embodiments, the protein load of the mixture comprising protein of interest is adjusted to a total protein load to the column of between about 50 and 1000 g/L, or between about 250 and 700 g/L, or between about 350 and 500 g/L. In certain embodiments, the protein concentration of the load protein mixture is adjusted to a protein concentration of the material loaded to the column of about 0.5 and 30 g/L, or between about 1 and 20 g/L, or between about 3 and 10 g/L.

In certain embodiments, aggregate concentration is measured and used to as a parameter for controlling aggregate clearance in the present invention. For example, but not by way of limitation, the data presented in the Examples below, supports the novel finding that aggregation concentration influences the aggregate reduction by hydrophobic interaction chromatography. Thus, in certain embodiments, the aggregate concentration is adjusted from about 0.5 to 0.1 g/L, to about 0.1 to 0.05 g/L or to below 0.05 g/L.

In certain embodiments, monomer concentration is measured and used to as a parameter for controlling aggregate clearance in the present invention. For example, but not by way of limitation, the data presented in the Examples below supports the novel finding that control of the concentration of the monomer can be used to achieve improved aggregate clearance. Thus, in certain embodiments, the monomer concentration is adjusted from about 15 to 8 g/L, to about 8 to 4 g/L or to below 4 g/L.

In certain embodiments, monomer and aggregate concentration is measured and used to as a parameter for controlling aggregate clearance in the present invention. For example, but not by way of limitation, the data presented in the Examples below supports the novel finding that control of the monomer and aggregate concentrations within certain ranges can be used to achieve improved aggregate clearance. Thus, in certain embodiments, the monomer concentration is adjusted from about 20 to 15 g/L, about 15 to 8 g/L or to below 4 g/L and the aggregate concentration is adjusted to 0.5 to 0.1 g/L, about 0.1 to 0.05 g/L or to below 0.05 g/L to achieve aggregate reduction in the present invention.

Because the pH selected for any particular purification process must be compatible with protein stability and activity, thus particular pH conditions may be specific for each application. However, because at pH 5-8.5, particular pH values have very little significance on the final selectivity and resolution of a HIC separation, such conditions may be favored. An increase in pH weakens hydrophobic interactions and retention of proteins changes more drastically at pH values above 8.5 or below 5.0. In addition, changes in ionic strength, the presence of organic solvents, temperature and pH (especially at the isoelectric point, pI, when there is no net surface charge) can impact protein structure and solubility and, consequently, the interaction with other hydrophobic surfaces, such as those in HIC media and hence, in certain embodiments, the present invention incorporates purification strategies wherein one or more of the foregoing are adjusted to achieve the desired reduction in process-related impurities and/or product-related substances.

In certain embodiments of the instant invention, control of molecular weight heterogeneity can be attained by purifying a protein of interest from a mixture comprising the protein with adsorbent material containing HIC functional group (also referred to as "HIC media") and an aqueous salt solution under loading conditions that permits both the protein of interest and non-target proteins to partially bind to the HIC adsorbent, and thereafter flowing through and washing off the protein of interest that is now reduced in aggregate species and impurities. In certain embodiments, such washing steps will employ similar conditions as the loading solution. In certain embodiments, product/process-related substances/impurities as well as bound protein with enhanced aggregate content can be eluted from the HIC adsorbent with a solution having a lower conductivity than the loading solution.

In certain embodiments, HIC chromatographic fractions are collected during the load, wash, and/or elution, and are combined after appropriate analysis to provide a protein preparation that contains the desired, e.g., reduced, level of aggregate species. In certain embodiments, the load pool is combined with certain wash fractions to improve the yield of the process while still achieving the desired, e.g., reduced, aggregate levels in the resulting material.

In certain embodiments, the wash step(s) employed in the context of HIC chromatography can be performed using conditions similar to the load conditions or alternatively by decreasing the conductivity of the wash in a step-wise or linear gradient manner.

In certain embodiments, spectroscopy methods such as UV, NIR, FTIR, Fluorescence, Raman may be used to monitor levels of aggregates and low molecular weight variants (e.g., fragments of the protein of interest) in an on-line, at-line or in-line mode, which can then be used to control the level of aggregates in the pooled material collected from the HIC adsorbent effluent. In certain embodiments, on-line, at-line or in-line monitoring methods can be used either on the effluent line of the chromatography step or in the collection vessel, to enable achievement of the desired product quality/recovery. In certain embodiments, the UV signal can be used as a surrogate to achieve an appropriate product quality/recovery, wherein the UV signal can be processed appropriately, including, but not limited to, such processing techniques as integration, differentiation, moving average, such that normal process variability can be addressed and the target product quality can be achieved. In certain embodiments, such measurements can be combined with in-line dilution methods such that ion concentration/conductivity of the load/wash can be controlled by feedback and hence facilitate product quality control.

In certain embodiments, a combination of HIC and AEX and CEX and MM methods can be used to prepare product-related aggregate- and/or fragment-reduced materials, including certain embodiments where one technology is used in a complementary/supplementary manner with another technology. In certain embodiments, such a combination can be performed such that certain sub-species are removed predominantly by one technology, such that the combination provides the desired final composition/product quality. In certain embodiments, such combinations include the use of additional intervening chromatography, filtration, pH adjustment, UF/DF steps so as to achieve the desired product quality, ion concentration, and/or viral reduction.

5.4.4 Affinity Chromatography

In certain embodiments, the sample matrix is subjected to affinity chromatography to purify the antibody of interest away from process-related impurities and/or product-related substances. As noted above, certain embodiments of the present in invention will employ one or more affinity chromatography steps prior to the HIC purification step, while others will employ an affinity chromatography step after or both before and after the HIC purification step. In certain embodiments, the affinity chromatography media is a Protein A, G, A/G, or L media, although alternative affinity chromatography medias are known in the art. There are a variety of commercial sources for Protein A media. Suitable medias include, but not limited to, MabSelect SuRe™, MabSelect SuRe LX, MabSelect, MabSelect Xtra, rProtein A Sepharose from GE Healthcare, ProSep HC, ProSep Ultra, and ProSep Ultra Plus from EMD Millipore, MapCapture from Life Technologies.

In certain embodiments, the Protein A column can be equilibrated with a suitable buffer prior to sample loading. Following the loading of the column, the column can be washed one or multiple times using a suitable sets of buffers. The Protein A column can then be eluted using an appropriate elution buffer. The eluate can be monitored using techniques well known to those skilled in the art. The eluate fractions of interest can be collected and then prepared for further processing.

The Protein A eluate may subject to a viral inactivation step either by detergent or low pH, provided this step is not performed prior to the Protein A capture operation. A proper detergent concentration or pH and time can be selected to obtain desired viral inactivation results. After viral inactivation, the Protein A eluate is usually pH and/or conductivity adjusted for subsequent purification steps.

The Protein A eluate may be subjected to filtration through a depth filter to remove turbidity and/or various impurities from the antibody of interest prior to additional chromatographic polishing steps. Examples of depth filters include, but not limited to, Millistak+X0HC, F0HC, D0HC, A1HC, and B1HC Pod filters (EMD Millipore), or Zeta Plus 30ZA/60ZA, 60ZA/90ZA, delipid, VR07, and VR05 filters (3M). The Protein A eluate pool may need to be conditioned to proper pH and conductivity to obtain desired impurity removal and product recovery from the depth filtration step.

5.4.5 Ion Exchange Chromatography

In certain embodiments, the instant invention provides methods for producing process-related impurity and/or product-related substance-reduced protein preparation from a mixture comprising a protein of interest (i.e., a product) and at least one process-related impurity and/or product-related substance by subjecting the mixture to at least one ion exchange separation step in addition to the HIC step described above. In certain embodiments, the ion exchange step will occur after the above-described Protein A affinity and/or HIC chromatography steps, such that an eluate comprising the protein of interest is obtained. In addition, an ion exchange separation step can be employed after the HIC purification step. As used herein, ion exchange separations includes any method by which two substances are separated based on the difference in their respective ionic charges, either on the protein of interest and/or chromatographic material as a whole or locally on specific regions of the protein of interest and/or chromatographic material, and thus can employ either cationic exchange material or anionic exchange material.

The use of a cationic exchange material versus an anionic exchange material is based on the local charges of the protein of interest in a given solution. Therefore, it is within the scope of this invention to employ an anionic exchange step prior to the use of a HIC step, or a cationic exchange step prior to the use of an HIC step. Furthermore, it is within the scope of this invention to employ only a cationic exchange step, only an anionic exchange step, or any serial combination of the two either prior to or subsequent to the HIC step.

In performing the separation, the antibody sample mixture can be contacted with the ion exchange material by using any of a variety of techniques, e.g., using a batch purification technique or a chromatographic technique, as described above in connection with HIC.

Ion exchange chromatography separates molecules based on differences between the local charges of the proteins of interest and the local charges of the chromatographic material. A packed ion-exchange chromatography column or an ion-exchange membrane device can be operated in a bind-elute mode, a flow-through, or a hybrid mode as discussed above in connection with HIC. After washing the column or the membrane device with the equilibration buffer or another buffer with different pH and/or conductivity, the product recovery is achieved by increasing the ionic strength (i.e., conductivity) of the elution buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). The column is then regenerated before next use.

Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate (S). Cellulose ion exchange medias such as DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow, and Capto™ S are all available from GE Healthcare. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa., or Nuvia S and UNOSphere™ S from BioRad, Hercules, Calif., Eshmuno® S from EMD Millipore, Billerica, Calif.

5.4.6 Mixed Mode Chromatography

The present invention also features methods for purifying a protein preparation from a mixture comprising a protein of interest comprising a mixed mode chromatography separation step. Mixed mode chromatography is chromatography that utilizes a mixed mode media, such as, but not limited to CaptoAdhere available from GE Healthcare. Such a media comprises a mixed mode chromatography ligand. In certain embodiments, such a ligand refers to a ligand that is capable of providing at least two different, but co-operative, sites which interact with the substance to be bound. One of these sites gives an attractive type of charge-charge interaction between the ligand and the substance of interest. The other site typically gives electron acceptor-donor interaction and/or hydrophobic and/or hydrophilic interactions. Electron donor-acceptor interactions include interactions such as hydrogen-bonding, $\pi$-$\pi$, cation-$\pi$, charge transfer, dipole-dipole, induced dipole etc. The mixed mode functionality can give a different selectivity compared to traditional anion exchangers. For example, CaptoAdhere is designed for post-Protein A purification of monoclonal antibodies, where removal of leached Protein A, aggregates, host cell proteins, nucleic acids and viruses from monoclonal antibodies is performed in flow-through mode (the antibodies pass directly through the column while the contaminants are adsorbed). Mixed mode chromatography ligands are also known as "multimodal" chromatography ligands.

In certain embodiments, the mixed mode chromatography media is comprised of mixed mode ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

5.4.7 Viral Filtration

Viral filtration is a dedicated viral reduction step in the entire purification process. This step is usually performed post chromatographic polishing steps. Viral reduction can be achieved via the use of suitable filters including, but not limited to, Planova 20N™, 50 N or BioEx from Asahi Kasei Pharma, Viresolve™ filters from EMD Millipore, ViroSart CPV from Sartorius, or Ultipor DV20 or DV50™ filter from Pall Corporation. It will be apparent to one of ordinary skill in the art to select a suitable filter to obtain desired filtration performance.

5.4.8 Ultrafiltration/Diafiltration

Certain embodiments of the present invention employ ultrafiltration and/or diafiltration steps to further purify and concentrate the antibody sample. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). A preferred filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 μm. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments, Microsolutes are removed most efficiently by adding solvent to the solution being ultrafiltered at a rate approximately equal to the ultratfiltration rate. This washes microspecies from the solution at a constant volume, effectively purifying the retained antibody. In certain embodiments of the present invention, a diafiltration step is employed to exchange the various buffers used in connection with the instant invention, optionally prior to further chromatography or other purification steps, as well as to remove impurities from the antibody preparations.

5.4.9 Exemplary Purification Strategies

In certain embodiments, primary recovery can proceed by sequentially employing pH reduction, centrifugation, and filtration steps to remove cells and cell debris (including HCPs) from the production bioreactor harvest. In certain embodiments, the present invention is directed to HIC purification steps where an HIC media partially binds antibody product as well as product-related substances/impurities and process-related impurities during the loading step with some antibody product collected during the loading step in the unbound fraction and when the column is subjected to a subsequent wash buffer with substantially similar composition, the antibody product reduced in the said impurities/substances are collected in the wash fraction. The antibody product in the flow through and wash fractions represent the purified or impurity reduced materials. The antibody product is specifically eluted while the product-related and process-related impurities are retained on the media. Examples of buffers that can be used in the context of both the loading and elution steps of the present invention include, but are not limited to, the following: about 0.1 M to about 0.6 M sodium citrate (NaCit), pH 5.6; or about 0.5 M to about 1.1 M ammonium sulfate (AmSO$_4$), pH 7.0 as well as buffers substantially similar, in that any differences are result in insubstantial changes to the elution of product-related or process-related impurities, yet retain the ability to elute antibody product. Such buffers can span a range of varying "hydrophobicities" based on the rationales discussed in section 4.4.3, above.

In certain embodiments, the HIC media employed in the HIC step is CaptoPhenyl (GE) resin. In certain embodiments, the CaptoPhenyl (GE) resin is buffer exchanged into 0.4 M sodium citrate (NaCit), pH 5.6, and then distributed in 100 μL aliquots into microcentrifuge tubes, Each tube is then challenged with 2 mL of antibody produce source material, e.g., a partially purified cell culture harvest sample, in 0.4 M NaCit, pH 5.6, at a range of concentrations from 0.5-15.0 mg/mL and incubated for 3 hours at room temperature with mixing. The resin is allowed to settle and the supernatant removed and replaced with 1 mL of fresh 0.4 M NaCit, pH 5.6, buffer and incubated for 2 hours at room temperature with mixing. This step was repeated one more time.

In alternative embodiments, the CaptoPhenyl (GE) HIC resin can be packed in 1.0 cm×10.0 cm (OmniFit) columns. Antibody product HIC-load can be prepared by diluting the source material, e.g., a partially purified cell culture harvest sample, with a 1.2 M stock solution of sodium citrate (NaCit), pH 5.6, to final concentration in the range of 0.3 to 0.5 M NaCit, pH 5.6. CaptoPhenyl columns can then be equilibrated with 7 column volumes (CVs) of a NaCit buffer, pH 5.6, corresponding to the load concentration. The antibody product solution can then be loaded to the column in the range of 200-500 g/L, after which the column is washed with 20 CVs of the equilibration buffer. The column can then be regenerated (3 CVs f 25 mM sodium phosphate/20% (v/v) isopropyl alcohol, pH 6.5), cleaned in place (3 CVs 1M NaOH, 60 min hold), and stored (5 CVs of 25 mM sodium phosphate/20% (v/v) isopropyl alcohol, pH 6.5). The effluent from the column can be fractionated during the entire run and used to monitor the breakthrough of both the antibody product monomer as well as product and process related impurities; namely aggregates and host cell protein (HCP).

Such HIC purification steps can be preceded by affinity chromatography, for example, but not limited to, the use of Protein A-base affinity chromatography. There are several commercial sources for Protein A media. One suitable media is MabSelect™ from GE Healthcare. An example of a suitable column packed with MabSelect™ is a column about 1.0 cm diameter× about 21.6 cm long (~17 mL bed volume). This size column can be used for bench scale. This can be compared with other columns used for scale ups. For example, a 20 cm×21 cm column whose bed volume is about 6.6 L can be used for commercial production. Regardless of the column, the column can be packed using a suitable media such as MabSelect™.

In certain aspects, the Protein A column can be equilibrated with a suitable buffer prior to sample loading. An example of a suitable buffer is a Tris/NaCl buffer, pH of about 6 to 8, and in certain embodiments about 7.2. A specific example of suitable conditions is 25 mM Tris, 100 mM NaCl, pH 7.2. Following this equilibration, the sample can be loaded onto the column. Following the loading of the column, the column can be washed one or multiple times using, e.g., the equilibrating buffer. Other washes including washes employing different buffers can be used before eluting the column. For example, the column can be washed using one or more column volumes of 20 mM citric acid/sodium citrate, 0.5 M NaCl at pH of about 6.0. This wash can optionally be followed by one or more washes using the equilibrating buffer. The Protein A column can then be eluted using an appropriate elution buffer. An example of a suitable elution buffer is an acetic acid/NaCl buffer, pH around 3.5. Suitable conditions are, e.g., 0.1 NI acetic acid, pH 3.5. The eluate can be monitored using techniques well known to those skilled in the art. For example, the absorbance at OD$_{280}$ can be followed. Column eluate can be collected starting with an initial deflection of about 0.5 AU to a reading of about 0.5 AU at the trailing edge of the elution peak. The elution fraction(s) of interest can then be prepared for further processing. For example, the collected sample can be titrated to a pH of about 5.0 using Tris (e.g., 1.0 M) at a pH of about 10. Optionally, this titrated sample can be filtered and further processed.

In certain embodiments, the HIC purification step can also be preceded by an ion exchange chromatography step. The ion exchange purification step can occur before, after, or in place of an affinity chromatography step. In certain embodiments, where a Protein A step precedes the ion exchange step, a Protein A eluate is purified using a cation exchange column. In certain embodiments, the equilibrating buffer used in the cation exchange column is a buffer having a pH of about 5.0. An example of a suitable buffer is about 210 mM sodium acetate, pH 5.0. Following equilibration, the column is loaded with sample prepared from HIC purification step above. The column is packed with a cation exchange media, such as CM Sepharose™ Fast Flow from GE Healthcare. The column is then washed using the equilibrating buffer. The column is next subjected to an elution step using a buffer having a greater ionic strength as compared to the equilibrating or wash buffer. For example, a suitable elution buffer can be about 790 mM sodium acetate, pH 5.0. The antibodies will be eluted and can be monitored using a UV spectrophotometer set at $OD_{280nm}$. In a particular example, elution collection can be from upside 3 $OD_{280nm}$ to downside 8 $OD_{280nm}$. It should be understood that one skilled in the art may vary the conditions and yet still be within the scope of the invention.

In certain embodiments where a Protein A step precedes an ion exchange step, a Protein A eluate is purified using an anion exchange column. A non-limiting example of a suitable column for this step is a 60 cm diameter×30 cm long column whose bed volume is about 85 L. The column is packed with an anion exchange media, such as Q Sepharose™ Fast Flow from GE Healthcare. The column can be equilibrated using about seven column volumes of an appropriate buffer such as Tris/sodium chloride. An example of suitable conditions is 25 mM Tris, 50 mM sodium chloride at pH 8.0. A skilled artisan may vary the conditions but still be within the scope of the present invention. The column is loaded with the collected sample from the HIC purification step outlined above. In another aspect, the column is loaded from the eluate collected during cation exchange. Following the loading of the column, the column is washed with the equilibration buffer (e.g., the Tris/sodium chloride buffer). The flow-through comprising the antibodies can be monitored using a UV spectrophotometer at $OD_{280nm}$. This anion exchange step reduces process related impurities such as nucleic acids like DNA, and host cell proteins. The separation occurs due to the fact that the antibodies of interest do not substantially interact with nor bind to the solid phase of the column, e.g., to the Q Sepharose™, but many impurities do interact with and bind to the column's solid phase. The anion exchange can be performed at about 12° C.

In certain embodiments, the cation exchange or anion exchange eluate, depending on which ion exchange step is employed, or employed first, is next filtered using, e.g., a 16 inch Cuno™ delipid filter. This filtration, using the delipid filter, can be followed by, e.g., a 30-inch 0.45/0.2 µm Sartopore™ bi-layer filter cartridge. The ion exchange elution buffer can be used to flush the residual volume remaining in the filters and prepared for ultrafiltration/diafiltration.

In order to accomplish the ultratfiltration/diafiltration step, the filtration media is prepared in a suitable buffer, e.g., 20 mM sodium phosphate, pH 7.0. A salt such as sodium chloride can be added to increase the ionic strength, e.g., 100 mM sodium chloride. This ultrafiltration/diafiltration step serves to concentrate the anti-IL-12, anti-TNFα, or anti-IL-18 antibodies, remove the sodium acetate and adjust the pH. Commercial filters are available to effectuate this step. For example, Millipore manufactures a 30 kD molecular weight cut-off (MWCO) cellulose ultrafilter membrane cassette. This filtration procedure can be conducted at or around room temperature.

In certain embodiments, the sample from the capture filtration step above is subjected to a second ion exchange separation step. In certain embodiments, this second ion exchange separation will involve separation based on the opposite charge of the first ion exchange separation. For example, if an anion exchange step is employed after HIC purification, the second ion exchange chromatographic step may be a cation exchange step. Conversely, if the HIC purification step was followed by a cation exchange step, that step would be followed by an anion exchange step. In certain embodiments the first ion exchange eluate can be subjected directly to the second ion exchange chromatographic step where the first ion exchange eluate is adjusted to the appropriate buffer conditions. Suitable anionic and cationic separation materials and conditions are described above.

In certain embodiments, a mixed mode chromatography step will precede the HIC chromatography step, thereby forming a mixed mode chromatography sample that can be exposed to the HIC media in the HIC chromatography step. Examples of mixed mode medias include, but are not limited to: CaptoAdhere (GE Healthcare), PPA-HyperCel (Pall Life Sciences), and HEA-HyperCel (Pall Life Sciences). In certain embodiments, the mixed mode chromatography step is a CaptoAdhere chromatography step. In certain embodiments, the mixed mode chromatography sample is further subject to a filtration step. Filters well known to those skilled in the art can be used in this embodiment. In one aspect, the filtration step is a nanofiltration step. In certain embodiments, a depth filtration step follows a filtration step.

In certain embodiments of the invention, the eluate from the hydrophobic chromatography step is subjected to filtration for the removal of viral particles, including intact viruses, if present. A non-limiting example of a suitable filter is the Ultipor DV50™ filter from Pall Corporation. Other viral filters can be used in this filtration step and are well known to those skilled in the art. The HIC eluate is passed through a pre-wetted filter of about 0.1 µm and a 2×30-inch Ultipor DV50™ filter train at around 34 psig. In certain embodiments, following the filtration process, the filter is washed using, e.g., the HIC elution buffer in order to remove any antibodies retained in the filter housing. The filtrate can be stored in a pre-sterilized container at around 12° C.

In a certain embodiments, the filtrate from the above is again subjected to ultrafiltration/diafiltration. This step is important if a practitioner's end point is to use the antibody in a, e.g., pharmaceutical formulation. This process, if employed, can facilitate the concentration of antibody, removal of buffering salts previously used and replace it with a particular formulation buffer. In certain embodiments, continuous diafiltration with multiple volumes, e.g., two volumes, of a formulation buffer is performed. A non-limiting example of a suitable formulation buffer is 5 mM methionine, 2% mannitol, 0.5% sucrose, pH 5.9 buffer (no Tween). Upon completion of this diavolume exchange the antibodies are concentrated. Once a predetermined concentration of antibody has been achieved, then a practitioner can calculate the amount of 10% Tween that should be added to arrive at a final Tween concentration of about 0.005% (v/v).

Certain embodiments of the present invention will include further purification steps. Examples of additional purification procedures which can be performed prior to, during, or following the ion exchange chromatography method include ethanol precipitation, isoelectric focusing, reverse phase HPLC, chromatography on silica, chromatography on heparin Sepharose™, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g., using protein G, an antibody, a specific substrate, ligand or antigen as the capture reagent).

In certain embodiments the unbound flow through and wash fractions can be further fractionated and a combination of fractions providing a target product purity can be pooled.

In certain embodiments the protein concentration can be adjusted to achieve a differential partitioning behavior between the antibody product and the product-related substances such that the purity and/or yield can be further improved.

In certain embodiments the loading can be performed at different protein concentrations during the loading operation to improve the product quality/yield of any particular purification step.

In certain embodiments the column temperature, can be independently varied to improve the separation efficiency and/or yield of any particular purification step.

In certain embodiments, the loading and washing buffer matrices can be different or composed of mixtures of chemicals, while achieving similar "hydrophobic interaction" behavior such that the above novel separation can be effected.

In certain embodiments, the loading and washing buffers can be different, in terms of ionic strength or pH, while remaining substantially similar in function in terms of the washout of the product achieved during the wash step.

In certain embodiments, the loading & washing steps can be controlled by in-line, at-line or off-line measurement of the product related impurity/substance levels, either in the column effluent, or the collected pool or both, so as to achieve the target product quality and/or yield.

In certain embodiments, the loading concentration can be dynamically controlled by in-line or batch or continuous dilutions with buffers or other solutions to achieve the partitioning necessary to improve the separation efficiency and/or yield.

In certain embodiments, additives such as amino acids, sugars, PEG, etc can be added to the load or wash steps to modulate the partitioning behavior to achieve the separation efficiency and/or yield.

In certain embodiments, the separation can be performed on any type of hydrophobic interaction media such as membranes, monoliths or depth filters that have hydrophobic interaction characteristics.

Mixed mode media can also be employed to enable this method, provided the same functionality is achieved by appropriately adjusting the column loading and/or washing conditions.

5.5. Methods of Assaying Sample Purity

5.5.1 Assaying Host Cell Protein

The present invention also provides methods for determining the residual levels of host cell protein (HCP) concentration in the isolated/purified antibody composition. As described above, HCPs are desirably excluded from the final target substance product. Exemplary HCPs include proteins originating from the source of the antibody production. Failure to identify and sufficiently remove HCPs from the target antibody may lead to reduced efficacy and/or adverse subject reactions.

As used herein, the term "HCP ELISA" refers to an ELISA where the second antibody used in the assay is specific to the HCPs produced from cells, e.g., CHO cells, used to generate the antibody of interest. The second antibody may be produced according to conventional methods known to those of skill in the art. For example, the second antibody may be produced using HCPs obtained by sham production and purification runs, i.e., the same cell line used to produce the antibody of interest is used, but the cell line is not transfected with antibody DNA. In an exemplary embodiment, the second antibody is produced using HPCs similar to those expressed in the cell expression system of choice, i.e., the cell expression system used to produce the target antibody.

Generally, HCP ELISA comprises sandwiching a liquid sample comprising HCPs between two layers of antibodies, i.e., a first antibody and a second antibody. The sample is incubated during which time the HCPs in the sample are captured by the first antibody, for example, but not limited to goat anti-CHO, affinity purified (Cygnus). A labeled second antibody, or blend of antibodies, specific to the HCPs produced from the cells used to generate the antibody, e.g., anti-CHO HCP Biotinylated, is added, and binds to the HCPs within the sample. In certain embodiments the first and second antibodies are polyclonal antibodies. In certain aspects the first and second antibodies are blends of polyclonal antibodies raised against HCPs. The amount of HCP contained in the sample is determined using the appropriate test based on the label of the second antibody.

HCP ELISA may be used for determining the level of HCPs in an antibody composition, such as an eluate or flow-through obtained using the process described above. The present invention also provides a composition comprising an antibody, wherein the composition has no detectable level of HCPs as determined by an HCP Enzyme Linked Immunosorbent Assay ("ELISA").

5.5.2 Assaying Charge and Size Variants

In certain embodiments, the levels of product-related substances, such as acidic species and other charge variants, in the chromatographic samples produced using the techniques described herein are analyzed. For example, but not by way of limitation, the acidic species and other charge variants present in the Adalimumab process samples can be quantified according to the following methods. Cation exchange chromatography was performed on a Dionex ProPac WCX-10, Analytical column 4 mm×250 mm (Dionex, CA). An Agilent 1200 HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

In certain embodiments, the levels of aggregates, monomer, and fragments in the chromatographic samples produced using the techniques described herein are analyzed. In certain embodiments, the aggregates, monomer, and fragments are measured using a size exclusion chromatographic (SEC) method for each molecule. For example, but not by way of limitation, a TSK-gel G3000SWxL, 5 µm, 125 Å, 7.8×300 mm column (Tosoh Bioscience) can be used in connection with certain embodiments, while a TSK-gel Super SW3000, 4 µm, 250 Å, 4.6×300 mm column (Tosoh Bioscience) can be used in alternative embodiments. In certain embodiments, the aforementioned columns are used along with an Agilent or a Shimazhu HPLC system. In certain embodiments, sample injections are made under isocratic elution conditions using a mobile phase consisting of, for example, 100 mM sodium sulfate and 100 mM sodium phosphate at pH 6.8, and detected with UV absorbance at 214 nm. In certain embodiments, the mobile phase will consist of 1×PBS at pH 7.4, and elution profile detected with UV absorbance at 280 nm. In certain embodiments, quantification is based on the relative area of detected peaks.

5.6. Further Modifications

The purified proteins, e.g., antibodies, of the present invention can be modified. In some embodiments, the proteins are chemically modified to provide a desired effect. For example, pegylation of antibodies or antibody fragments of the invention may be carried out by any of the pegylation reactions known in the art, as described, e.g., in the following references: Focus on Growth Factors 3:4-10 (1992); EP 0 154 316; and EP 0 401 384, each of which is incorporated by reference herein in its entirety. In one aspect, the pegylation is carried out via an acylation reaction or an alkylation reaction with a reactive polyethylene glycol molecule (or an analogous reactive water-soluble polymer). A suitable water-soluble polymer for pegylation of the antibodies and antibody fragments of the invention is polyethylene glycol (PEG). As used herein, "polyethylene glycol" is meant to encompass any of the forms of PEG that have been used to derivative other proteins, such as mono(C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under suitable conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

An antibody of the invention can be derivatized or linked to another functional molecule (e.g., another peptide or protein). Far example, an antibody of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody of the invention may be derivatized include fluorescent compounds. Exemplary fluorescent detectable agents include fluorescein, fluorescein isothiocyanate, rhodamine, 5-dimethyl amine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

5.7. Pharmaceutical Compositions

The proteins of interest, e.g., antibodies and antibody-binding portions thereof, of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is desirable to include isotonic agents, e.g., sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody.

The antibodies and antibody-binding portions thereof, of the invention can be incorporated into a pharmaceutical composition suitable for parenteral administration. The antibody or antibody-portions can be prepared as an injectable solution containing, e.g., 0.1-250 mg/mL antibody. The injectable solution can be composed of either a liquid or lyophilized dosage form in a flint or amber vial, ampule or pre-filled syringe. The buffer can be L-histidine approximately 1-50 mM, (optimally 5-10 mM), at pH 5.0 to 7.0 (optimally pH 6.0). Other suitable buffers include but are not limited to sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

In one aspect, the pharmaceutical composition includes the antibody at a dosage of about 0.01 mg/kg-10 mg/kg. In another aspect, the dosages of the antibody include approximately 1 mg/kg administered every other week, or approximately 0.3 mg/kg administered weekly. A skilled practitioner can ascertain the proper dosage and regime for administering to a subject.

The compositions of this invention may be in a variety of forms. These include, e.g., liquid, semi-solid and solid dosage forms, such as liquid, solutions (e.g., injectable and infusible solutions), dispersions or suspensions, tablets, pills, powders, liposomes and suppositories. The form depends on, e.g., the intended mode of administration and therapeutic application. Typical compositions are in the form of injectable or infusible solutions, such as compositions similar to those used for passive immunization of humans with other antibodies. One mode of administration is parenteral (e.g., intravenous, subcutaneous, intraperitoneal, intramuscular). In one aspect, the antibody is administered by intravenous infusion or injection. In another aspect, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the methods of preparation are vacuum drying and spray-drying that yields a powder of the active ingredient plus any additional desired ingredient from a previously sterile-filtered solution thereof. The proper fluidity of a solution can be maintained, e.g., by the use of a coating such as lecithin, by the maintenance of the required particle size in the case of dispersion and by the use of surfactants. Prolonged absorption of injectable compositions can be brought about by including in the composition an agent that delays absorption, e.g., monostearate salts and gelatin.

The antibodies and antibody-binding portions thereof, of the present invention can be administered by a variety of methods known in the art, one route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978, the entire teaching of which is incorporated herein by reference.

In certain aspects, an antibody or antibody-binding portion thereof, of the invention may be orally administered, e.g., with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain aspects, an antibody or antibody-binding portion thereof, of the invention is co-formulated with and/or co-administered with one or more additional therapeutic agents that are useful for treating disorders. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect).

It should be understood that the antibodies of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition, e.g., an agent which affects the viscosity of the composition.

6. EXAMPLES

6.1. Materials & Methods

6.1.1. Chromatography Method

Except where noted, the materials and methods described in connection with the instant example were also employed in the examples of Sections 6.2., 6.3., and 6.4., below.

Pre-packed media columns were used in the following experiments, except where specified. The column was equilibrated in a buffer system with appropriate pH and conductivity. The column load was prepared from Protein A affinity chromatography eluates or concentrated CEX chromatography elutes by buffer exchange (if the eluates were with different buffer components from the mixed mode target buffer system) or addition of the stock solutions and/or water to obtain the target pH and conductivity as specified (if the eluates were with the same buffer components as the mixed mode target buffer system). The prepared load material was filtered and loaded on the column according to the target load amount (g protein/L media) as specified followed by washing with the equilibration buffer or buffer similar to equilibration buffer with volumes as specified. The column Flow Through/Wash were collected as fractions or as a pool. HIC column was cleaned with 20% Isopropyl Alcohol solution. 1M NaOH solution was used for column cleaning.

6.1.2. Buffer Preparation Method

Buffers were prepared targeting a specific salt concentration in a buffered system, and titrating to a specific pH with the conjugate acid or base. For example, an 800 mM Ammonium Sulfate ($AmSO_4$) pH 7.0 solution was made by dissolving AmSO4 salt in a 20 mM Tris-Acetate buffered solution, titrating with acetate, and subsequently bringing up to volume with water to achieve the desired $AmSO_4$ concentration. Load samples were prepared targeting a specific salt concentration by addition of concentrated salt solution in a buffered system, and titrating to a specific pH with the conjugate acid or base. For example, an 800 mM AmSO4 pH 7.0 load was made by mixing the load in a 1:1 ratio with a 1600 mM AmSO4 pH 7.0 stock buffer in a 40 mM Tris-Acetate, and subsequently titrating with Tris or acetate to achieve a final pH 7.0.

6.1.7. Size Exclusion Chromatography

The molecular weight distribution of collected samples were quantified according to the following methods. Size exclusion chromatography (SEC) was performed using a TSK-gel G3000SWxL, 5 μm, 125 Å, 7.8×300 mm column (Tosoh Bioscience) on an HP Agilent HPLC system. Injections were made under isocratic elution conditions using a mobile phase of 200 mM sodium sulfate, 100 mM sodium phosphate, pH 6.8, and detected with absorbance at 214 nm. Quantification is based on the relative area of detected peaks.

6.1.8. Host Cell Protein (HCP) ELISA

HCP assay is based on process specific antigen based ELISA. Sample dilutions were applied to achieve readings within the calibration range. The limit of quantitation of the assay is 0.625 ng/mL.

6.1.9. UV Spectroscopy $A_{280}$

UV A280 was used to determine protein concentrations for the samples post protein A elution. The assay was performed on an Agilent UV Spectrophotometer following the method. The protein concentration was determined using Beer-Lambert's Law, $A=\epsilon lc$, where A is Absorbance, $\epsilon$ is the extinction coefficient, l is the path length, and c is the concentration. The absorbance was taken at 280 nm, the path length was 1 cm, and the extinction coefficients were 1.39 for Adalimumab, 1.38 for mAb B, and 1.43 for mAb C.

6.2. Example HIC 1

Determining Operating Conditions Appropriate for an mAb:Media:Buffer Combination The demonstration of the current invention for a specific antibody & media is provided in this example, and consists of
1. Choosing a salt concentration that allows product and impurities to bind at a given pH.
2. Loading a small amount of protein to the column and then performing a linear gradient elution by decreasing the salt concentration.
3. Determining salt concentration range in which the protein elutes from the hydrophobic interaction media.

Figure 1:
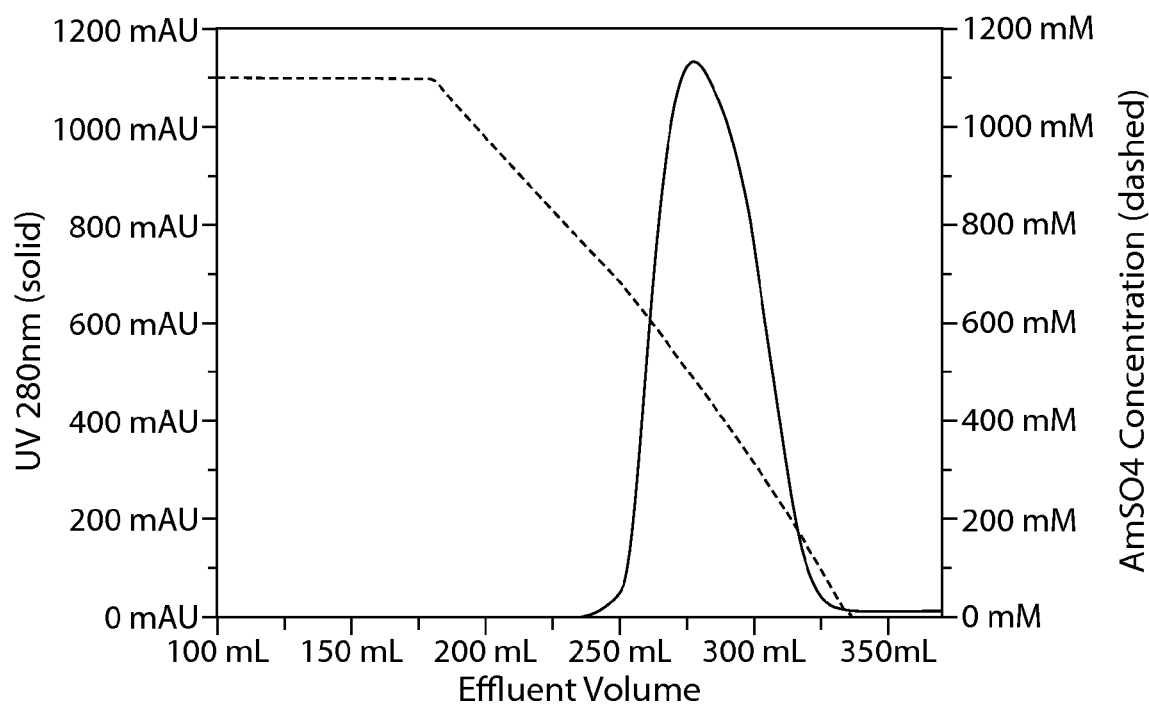

In this example, adalimumab and GE CaptoPhenyl were chosen. The column was equilibrated at 1.1 M AmSO$_4$ pH 7.0 (Tris/Acetate) for 10 CVs. Adalimumab was prepared at 1.1 M AmSO$_4$ and loaded to the column at 20 g-protein/L of resin. The column was washed with 10 CVs of the equilibration buffer. A linear gradient from 1.1M to 0M AmSO$_4$ pH 7.0 (Tris/Acetate) over 20CVs was performed. The process chromatogram is shown in FIG. 1.

This process can be repeated for any given mAb-media combination for a given buffer system. Table 1 shows the DOE parameters determined using the method described above for adlimumab in AmSO4 pH 7.0 (Tris/acetate) for 3 different HIC adsorbents.

TABLE 1

Example Experimental Design Scope determined from LGE with different resins
Adlimumab - Ammonium Sulfate pH 7.0 (Tris/Acetate)

| Resin | Buffer Concentration Range |
|---|---|
| Tosoh Hexyl | 250-750 mM |
| GE CaptoPhenyl | 300-650 mM |
| GE Butyl FF | 800-950 mM |

In practicing the current invention, the aggregate reduction desired can be achieved by appropriate pooling of the load and wash fractions. By collecting and subsequently determining the product quality of each fraction throughout the load and wash, the accumulative aggregate reduction and accumulative yield can be calculated using the weighted averages up to a given fraction. Additionally, the instantaneous yield can be estimated by comparing the protein recovered against the total protein loaded to the column at a given fraction. Sample calculations are shown below:

Sample Calculation A: Accumulative Yield Up to a Given Fraction $$\text{Accumulative Yield} = \frac{\text{Accumulated Protein Mass Recovered up to Fraction}}{\text{Total Mass Protein Load}}$$

Sample Calculation B: Accumulative Aggregate Reduction Up to a Given Fraction $$\text{Accumulative Aggregate Reduction} = \text{Load } Agg \% - \frac{\text{Accumulated Aggregate Mass Recovered up to Fraction}}{\text{Accumulated Total Protein Mass Recovered up to Fraction}}$$

Sample Calculation C: Instantaneous Yield Up to a Given Fraction $$\text{Instantaneous Yield} = \frac{\text{Accumulated Protein Mass Recovered up to Fraction}}{\text{Total Protein Mass Loaded to Column at Fraction}}$$

The demonstration of the current invention for a specific antibody & resin is provided in this example, and consists of
1. For a given salt concentration and optionally pH and hydrophobic interaction media.
2. Loading the hydrophobic interaction media in excess of the dynamic binding capacity for the product for the given condition.
3. Washing the column with a buffer containing a similar salt concentration and optionally pH used for the equilibration and loading steps.
4. Collecting fractions throughout the loading and wash steps and subsequently determining the product quality profile (e.g. Aggregate, HCP etc.)

Figure 2:
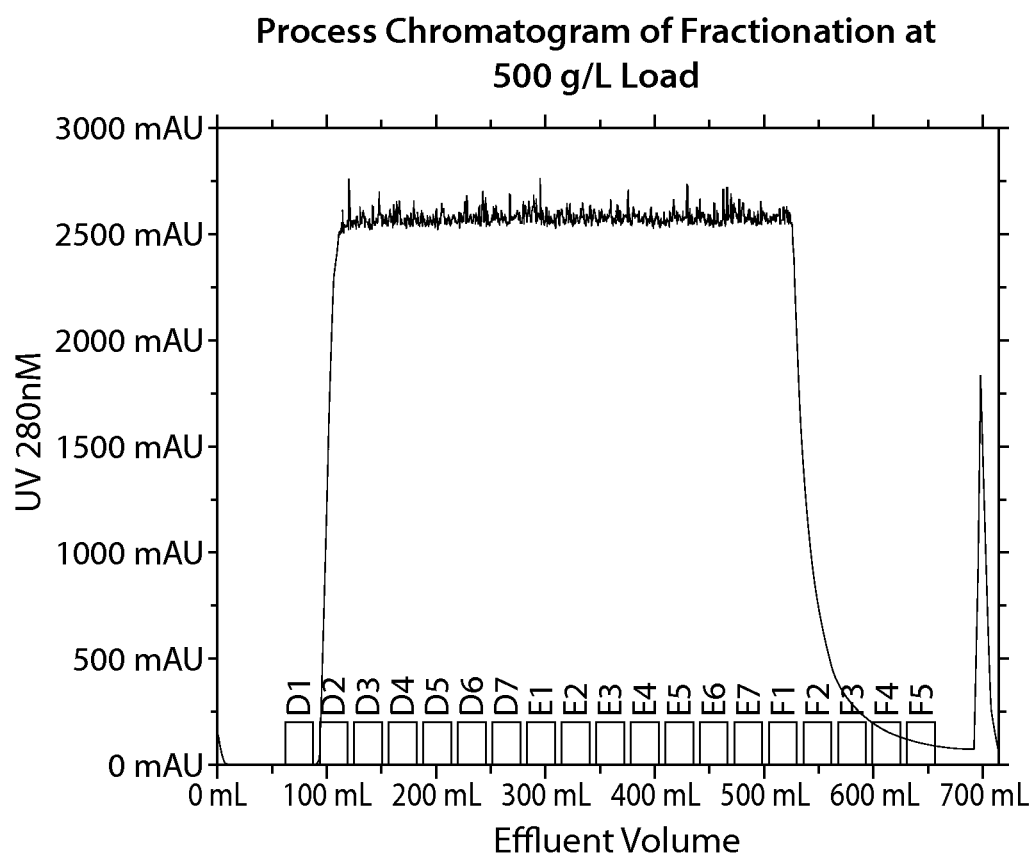

In this example, adalimumab and GE CaptoPhenyl were chosen. The experiment was performed at 400 mM sodium citrate (NaCit) pH 5.6. The column was equilibrated with 400 mM NaCit pH 5.6 for 10 CVs. Adalimumab was prepared at 400 mM NaCit pH 5.6 and loaded to the column at 500 g-protein/L-resin. The column was washed with 7 CVs of the equilibration buffer. The process chromatogram is shown in FIG. 2. Fractions were collected and analyzed for product quality and the accumulative yield and accumulative aggregate reduction calculated, shown in Table 2. From this example, it is clear to one skilled in the art to determine a run condition which delivers a targeted product quality and/or step yield.

This general approach is used to evaluate the performance for a given operating condition for any resin/mAb/buffer combination.

TABLE 2

Accumulative Yield and AR Reduction from FIG. 2

| Fraction | Load | Accumulative Recovery | Accumulative ΔAgg |
|---|---|---|---|
| D1 | 8 g/L | 0% | 0.82% |
| D2 | 45 g/L | 4% | 0.77% |
| D3 | 82 g/L | 12% | 0.71% |
| D4 | 119 g/L | 19% | 0.67% |
| D5 | 156 g/L | 26% | 0.62% |
| D6 | 193 g/L | 33% | 0.56% |
| D7 | 231 g/L | 41% | 0.51% |
| E1 | 268 g/L | 48% | 0.47% |
| E2 | 305 g/L | 55% | 0.43% |
| E3 | 342 g/L | 62% | 0.40% |
| E4 | 379 g/L | 70% | 0.37% |
| E5 | 416 g/L | 77% | 0.34% |
| E6 | 454 g/L | 84% | 0.32% |
| E7 | 491 g/L | 91% | 0.29% |
| F1 | 500 g/L | 93% | 0.29% |
| F2 | WASH | 99% | 0.28% |
| F3 | WASH | 100% | 0.28% |
| F4 | WASH | 101% | 0.29% |
| F5 | WASH | 101% | 0.29% |

6.3. Example HIC 2

Demonstration of Aggregate Reduction with HIC Resins

This data set is compiled to demonstrate the aggregate reduction achieved with six different HIC adsorbents. Each resin was evaluated with a 500 g/L load of adalimumab at a NaCit concentration near, and slightly higher than, the peak elution concentration determined from the process outlined in Example 6.2. Table 3 outlines the results from these experiments.

TABLE 3

Effect of HIC Resins on aggregate reduction of Adalimumab

| HIC Resin | NaCit, pH 5.6 | ΔAgg | Yield |
|---|---|---|---|
| Butyl | 400 mM | 1.5% | 99.8% |
|  | 450 mM | 1.2% | 85.7% |
| Hexyl | 240 mM | 1.2% | 93.9% |
|  | 300 mM | 1.1% | 100.9% |
| Phenyl | 400 mM | 1.5% | 96.5% |
|  | 450 mM | 1.2% | 90.7% |
| Octyl | 350 mM | 0.4% | 98.5% |
|  | 400 mM | 0.1% | 103.3% |
| GE Butyl FF | 550 mM | 1.2% | 88.1% |
|  | 600 mM | 1.7% | 83.0% |
| PPG | 450 mM | 0.2% | 97.5% |
|  | 600 mM | 1.0% | 38.1% |

6.4. Example HIC 3

Demonstration of Aggregate Reduction with Other Antibodies, mAb B and mAb C

Aggregate reduction technology of the current invention has been demonstrated with multiple antibodies using HIC adsorbents. Antibodies have different hydrophobic properties, leading to interaction behavior on a HIC column that differs from one antibody to another. Therefore the impact of salt type and concentration is different for each antibody.

Table 4 and Table 5, presented below, provide the data obtained for mAb B and mAB C. The data clearly demonstrates that the aggregate reduction technology is effective for alternatives to adalimumab.

TABLE 4

AR reduction for mAb B, pI~9.1

| HIC Resin | AmSO4, pH 5.0 | ΔAgg | Yield |
|---|---|---|---|
| Hexyl | 370 mM | 0.8% | 100% |
|  | 710 mM | 0.6% | 93% |
| Phenyl | 340 mM | 0.6% | 95% |
|  | 790 mM | 0.5% | 95% |
| Butyl | 840 mM | 0.6% | 99% |
|  | 1000 mM | 0.6% | 96% |

TABLE 5

AR reduction for mAb C, pI~7.0

| HIC Resin | AmSO4, pH 5.0 | ΔAgg | Yield |
|---|---|---|---|
| Hexyl | 80 mM | 5.0% | 89.0% |
|  | 330 mM | 4.5% | 99.8% |
| Phenyl | 130 mM | 3.5% | 92.8% |
|  | 480 mM | 2.9% | 92.8% |
| Butyl | 690 mM | 5.2% | 93.5% |
|  | 880 mM | 5.4% | 87.9% |

6.5. Example HIC 4

Demonstration of Aggregate Reduction with Different Salt Concentrations—Adalimumab Ion concentration is a key variable in the performance of hydrophobic interaction chromatography. For every combination of antibody/resin/pH there is a range of ion concentrations that provide aggregate reduction; the strategy outlined in Example 6.2. can be followed to determine the aggregate reduction and the corresponding recovery for each salt concentration.

Table 6, below, shows the effect of salt concentration on aggregate reduction and step yield. In this example CaptoPhenyl and adalimumab were chosen, and evaluated at a loading of 200-500 g/L in NaCit pH 5.6 at the concentration specified. The data demonstrates that the aggregate reduction can be effectively achieved over a range of salt concentrations, and that the salt concentration and column loading can be balanced to achieve a desired step yield and final product quality

TABLE 6

Effect of Ion Concentration on Aggregate Reduction

| NaCit pH 5.6 | Load | Yield | ΔAgg |
|---|---|---|---|
| 300 mM | 200 g/L | 92% | 0.59% |
|  | 350 g/L | 96% | 0.33% |
|  | 500 g/L | 97% | 0.24% |
| 400 mM | 200 g/L | 90% | 0.76% |
|  | 350 g/L | 94% | 0.43% |
|  | 500 g/L | 96% | 0.35% |
| 500 mM | 200 g/L | 85% | 1.09% |
|  | 350 g/L | 91% | 0.97% |
|  | 500 g/L | 94% | 0.86% |

6.6. Example HIC 5

Demonstration of Aggregate Reduction with Different Buffer Systems with Adalimumab In addition to the salt concentration, the salt anion and cation types are key variables in hydrophobic interaction chromatography. The invention has been demonstrated with ammonium sulfate, sodium sulfate, and sodium citrate. As one skilled in the art would appreciate the optimal salt concentration and optionally pH are different for each salt type and was derived by using the strategy outlined in Example 6.2. Table 7 shows the data of aggregate reduction and corresponding recovery for the different anion/cation types and different HIC adsorbents.

TABLE 7

Effect of Anion/Cation Type Aggregate Reduction

| Resin | Buffer System | Load | Yield | ΔAgg |
|---|---|---|---|---|
| CaptoPhenyl | 630 mM AmSO4 pH 7.0 | 300 g/L | 95% | 2.1% |
| | 300 mM AmSO4 pH 7.0 | 300 g/L | 99% | 1.1% |
| | 425 mM NaSO4 pH 7.0 | 300 g/L | 95% | 1.9% |
| | 240 mM NaSO4 pH 7.0 | 300 g/L | 101% | 1.1% |
| | 500 mM NaCit pH 5.6 | 350 g/L | 91% | 1.0% |
| | 300 mM NaCit pH 5.6 | 350 g/L | 96% | 0.2% |
| Tosoh Hexyl | 725 mM AmSO4 pH 7.0 | 300 g/L | 94% | 1.7% |
| | 275 mM AmSO4 pH 7.0 | 300 g/L | 103% | 0.9% |
| | 460 mM NaSO4 pH 7.0 | 300 g/L | 97% | 0.7% |
| | 180 mM NaSO4 pH 7.0 | 300 g/L | 101% | 0.6% |
| | 440 mM NaCit pH 5.6 | 300 g/L | 87% | 0.5% |
| | 150 mM NaCit pH 5.6 | 300 g/L | 97% | 0.5% |
| Butyl FF | 800 mM AmSO4 pH 7.0 | 300 g/L | 100% | 0.7% |
| | 1000 mM AmSO4 pH 7.0 | 300 g/L | 94% | 1.6% |
| | 750 mM NaSO4 pH 7.0 | 300 g/L | 96% | 1.8% |
| | 700 mM NaSO4 pH 7.0 | 300 g/L | 101% | 1.7% |
| | 700 mM NaCit pH 5.6 | 300 g/L | 98% | 1.6% |
| | 600 mM NaCit pH 5.6 | 300 g/L | 95% | 1.5% |

6.7. Example HIC 6

Demonstration of Aggregate Reduction with Different Loading

Furthermore, the strategy outlined in Example 6.2. to reduce aggregates through careful control of ion concentration, ion type, HIC adsorbent, and pH can be applied to various ranges of protein loading. Aggregate reduction for a range of protein loadings (e.g. 250-700 g/L) for CaptoPhenyl using a 400 mM NaCit pH 5.6 buffer is shown in Table 8, displaying a robust aggregate reduction across an expansive loading range.

TABLE 8

Impact of Column loading

| Load | Yield | ΔAgg | ΔAgg/LoadAgg |
|---|---|---|---|
| 250 g/L | 95% | 0.29% | 87% |
| 500 g/L | 100% | 0.25% | 77% |
| 700 g/L | 100% | 0.21% | 65% |

6.8. Example HIC 7

Figure 3:
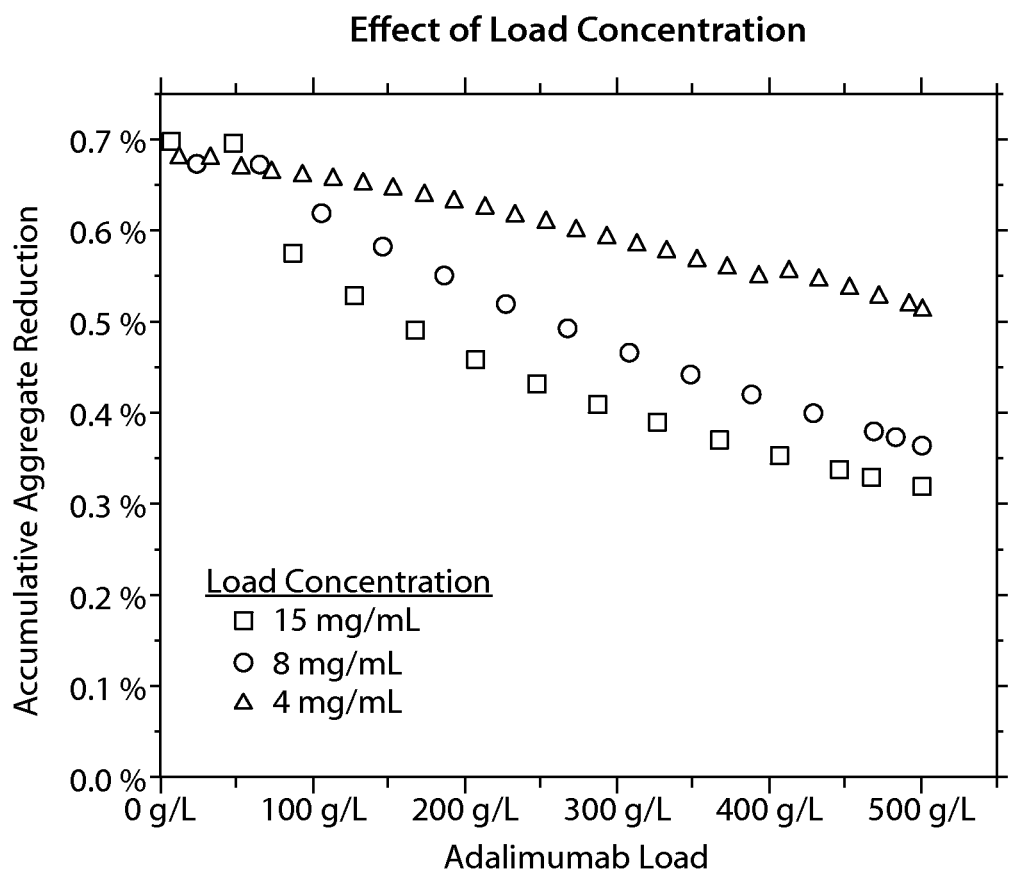
FIG. 3 depicts results of an experiment wherein a feed stream was serial diluted to cover a range of load concentrations from 4 to 15 mg/mL and loaded at 500 g/L to a CaptoPhenyl column in 400 mM NaCit pH 5.6; the results indicate the impact that the concentration of loaded protein can have on aggregate reduction.

Demonstration of Aggregate Reduction with Different Load Concentration—Adalimumab In addition to the strategy outlined in Example 6.7. to reduce aggregates through careful control of ion concentration, ion type, and HIC adsorbent, it has been shown that the concentration of the load protein can have an effect on aggregate reduction. In this example, a feed stream was serial diluted to cover a range of load concentrations from 4 to 15 mg/mL and loaded at 500 g/L to a CaptoPhenyl column in 400 mM NaCit pH 5.6. The effect of decreasing the concentration of the load protein is shown in FIG. 3.

6.9. Example HIC 8

Demonstration of HCP Reduction in Addition to Aggregate Reduction

HIC chromatography can also be effective in reducing host cell protein (HCP) levels. In the present invention, it has been demonstrated that HCP levels can be effectively reduced under operating conditions selected for aggregate reduction.

Table 9 shows HCP removal achieved along with aggregate reduction. The data clearly shows that other process related substances/impurities can be achieved using the current invention on the HIC adsorbents, and hence functions as an effective polishing step in the large scale purification of monoclonal antibodies.

TABLE 9

HCP Removal during HIC Chromatography

| NaCit pH 5.6 | Load | Yield | ΔAgg | HCP Load | HCP Pool |
|---|---|---|---|---|---|
| 300 mM | 200 g/L | 92% | 0.59% | 1398 ng/mg | NA |
| | 350 g/L | 96% | 0.33% | | 150 ng/mg |
| | 500 g/L | 97% | 0.24% | | 348 ng/mg |
| | 200 g/L | 99% | 0.34% | 38 ng/mg | 5 ng/mg |
| 400 mM | 200 g/L | 90% | 0.76% | 1599 ng/mg | 104 ng/mg |
| | 350 g/L | 94% | 0.43% | | 148 ng/mg |
| | 500 g/L | 96% | 0.35% | | 350 ng/mg |
| | 350 g/L | 97% | 0.35% | 38 ng/mg | 6 ng/mg |
| 500 mM | 200 g/L | 85% | 1.09% | 1528 ng/mg | 169 ng/mg |
| | 350 g/L | 91% | 0.97% | | 203 ng/mg |
| | 500 g/L | 94% | 0.86% | | 301 ng/mg |
| | 500 g/L | 87% | 0.35% | 38 ng/mg | 11 ng/mg |

6.10. Example HIC 9

Demonstration of Impact of Dynamic and Equilibrium Binding

In the HIC-based separation strategies described herein, the measured dynamic binding capacity (DBC), which is conventionally measured at 10% breakthrough, was found to be greater than the amount of protein that remained bound after washing the column (a.k.a equilibrium binding capacity, EBC) with a buffer with similar pH and salt concentration to the equilibration and load conditions. For example, but not by way of limitation, FIG. 4 shows an example of the DBC and EBC for the data presented in FIG. 2. In addition, Table 10 shows effect of salt type, concentration, and HIC resin on DBC and EBC values for Adalimumab.

TABLE 10

Comparison of DBC and EBC values for Adilmumab

| Resin | Buffer System | ΔAgg | DBC | EBC |
|---|---|---|---|---|
| CaptoPhenyl | 630 mM AmSO4 pH 7.0 | 2.1% | 27 g/L | 16 g/L |
| | 300 mM AmSO4 pH 7.0 | 1.1% | 6 g/L | 4 g/L |
| | 425 mM NaSO4 pH 7.0 | 1.9% | 22 g/L | 15 g/L |
| | 240 mM NaSO4 pH 7.0 | 1.1% | 6 g/L | 4 g/L |
| Butyl FF | 1000 mM AmSO4 pH 7.0 | 1.6% | 17 g/L | 11 g/L |
| | 800 mM AmSO4 pH 7.0 | 0.7% | 4 g/L | 4 g/L |
| | 750 mM NaSO4 pH 7.0 | 1.8% | 29 g/L | 13 g/L |
| | 700 mM NaSO4 pH 7.0 | 1.7% | 22 g/L | 11 g/L |

TABLE 10-continued

Comparison of DBC and EBC values for Adilmumab

| Resin | Buffer System | ΔAgg | DBC | EBC |
|---|---|---|---|---|
|  | 700 mM NaCit pH 5.6 | 1.6% | 39 g/L | 24 g/L |
|  | 600 mM NaCit pH 5.6 | 1.5% | 17 g/L | 11 g/L |

6.11. Example HIC 10

Combinations of HIC with Alternative Separation Strategies

The methods described herein for reducing aggregates using HIC can be used as an independent operation or in combination with other process steps that provide additional aggregate reduction or those providing additional complementary and supplementary purification. Data for specific separation strategies is provided in Tables 11 and 12. For example, but not by way of limitation, the following process combinations can be used:
1. Affinity→HIC
2. Affinity→AEX→HIC
3. Affinity→Mixed Mode→HIC

TABLE 11

Aggregate reduction with different source materials

| Load Source | Buffer Condition | Load | Yield | ΔAgg | HCP LRF |
|---|---|---|---|---|---|
| ProteinA | 400 mM NaCit pH 5.6 | 500 g/L | 96% | 1.49% | NA |
| Eluate | 450 mM NaCit pH 5.6 | 500 g/L | 91% | 1.22% | NA |
| ProteinA/ | 300 mM NaCit pH 5.6 | 200 g/L | 92% | 0.59% | 1.0 |
| AEX FTW | 400 mM NaCit pH 5.6 | 350 g/L | 94% | 0.43% | 1.0 |
|  | 500 mM NaCit pH 5.6 | 500 g/L | 94% | 0.86% | 0.7 |
| ProteinA/ | 300 mM NaCit pH 5.6 | 200 g/L | 99% | 0.34% | 0.8 |
| Mixed Mode | 400 mM NaCit pH 5.6 | 350 g/L | 97% | 0.35% | 0.8 |
| FTW | 500 mM NaCit pH 5.6 | 500 g/L | 87% | 0.35% | 0.5 |

TABLE 12

Complete Process Train with Protein A Capture - AR, HMW and HCP reduction

| Process | Yield (%) | % HMW reduction | HCP LRF |
|---|---|---|---|
| Clarified Harvest | 97.00% | n/a | n/a |
| Prt-A Eluate Pool | 89.60% | n/a | 1.87 |
| Viral Inactivated Filtrate | 99.70% | 0.07 | 0.39 |
| MM FT pool | 91.90% | 0.83 | 1.63 |
| HIC FT-pool | 98.50% | 0.23 | 0.46 |
| VF(FT) Filtrate | 96.10% | No reduction | 0.1 |
| BDS (FT) | 103.80% | No reduction | 0.13 |

6.12. Example HIC 11

Hybrid HIC Binding Mechanism

By estimating the partitioning coefficient $K_p$, it can be demonstrated that certain strategies described in the instant application do not fall under the category of "Weak-Partitioning (WP)" or "Flow-Through Overload (FT)" modes as those are described in the art, e.g., US2007/0060741. For example, FIG. 5A-B depict the results of experiments wherein aliquots of resin are incubated with a load covering a range of protein concentrations at room temperature for 3 hours, after which the protein solution is then removed, and replaced with equilibration buffer (Wash simulation) and incubated at room temperature for 3 hours (repeated, Wash II). After each incubation, the concentration of the protein solution is measured and used to calculated the amount of protein ((A) monomer D2E7, a.ka. Adalimumab, and (B) aggregate D2E7) bound to the resin (g protein/L resin) and plotted against the concentration of the protein solution at the end of the incubation (e.g. equilibrium).

FIG. 6A-B depict the results outlined in FIGS. 5A-B, highlighting the fact that at initial equilibrium a significant amount of monomer/aggregate is bound to the resin. However, after the protein solution is replaced with equilibration buffer (see arrow), the monomer de-sorbs from the resin and back into solution, where as the aggregate remains bound.

FIG. 7A-B depict a determination of the binding monomer and aggregate D2E7 (based on data provided in FIGS. 5A-B) by fitting the experimental equilibrium binding data to the Langmuir Isotherm using the equation: $q=(q_{max} \times C_{equil})/(K_d + C_{equil})$; where q=amount of protein bound to resin [=] g/L-resin; $q_{max}$=maximum amount of protein bound to resin [=] g/L-resin; $C_{equil}$=solution concentration of protein [=] g/L-soln; and $K_d$=equilibrium dissociation constant.

By fitting the experimental data, the $q_{max}$ and $K_d$ for the monomer and the aggregates can be calculated.

| Species | $Q_{max}$[mg/mL] | $K_d$[mg/mL] |
|---|---|---|
| Monomer | 41.9 | 0.47 |
| Aggregate | 6.0 | 0.01 |

Significantly, $q_{max}$ for both monomer/aggregate and the $K_d$ values (i.e. strength of binding) are similar to those of strong hydrophobic interactions, therefore it is not expected for this interaction to be "reversible." In addition, by calculating $K_p$ where:

| Species | $Q_{max}$ [mg/mL] | $K_d$ [mg/mL] | $K_p \equiv \dfrac{Q}{C} \cong \dfrac{Q_{max}}{K_d}$ |
|---|---|---|---|
| Monomer | 41.9 | 0.47 | 90 |
| Aggregate | 6.0 | 0.01 | 600 | it is apparent that the instant technique does not fail within the category of flow-through (where $K_p \leq 1$) or weak portioning (where $K_p = 1-10$), but rather fall within the category of bind and elute (where $K_p \geq 10$).

Patents, patent applications, publications, product descriptions, GenBank Accession Numbers, and protocols that may be cited throughout this application, the disclosures of which are incorporated herein by reference in their entireties for all purposes. For example, but not by Paienis. paicnl applications, publications, product descriptions, GenBank Accession Numbers, and protocols that may be cited throughout this application, the disclosures of which are incorporated herein by reference in their entireties for all purposes. For example, but not by way of limitation, U.S. Patent Application No: 13/803,808, filed on Mar. 14, 2013; U.S. Patent Application No: 13/830,583, filed on Mar. 14, 2013; U.S. Patent Application No: 13/829,989, filed on Mar. 14, 2013; U.S. Patent Application No: 13/830,976, filed on Mar. 14, 2013; and U.S. Patent Application No: 13/804,220, filed on Mar. 14, 2013 are incorporated herein by reference in their entireties for all purposes.

What is claimed is:
1. A method for producing a preparation comprising a protein of interest and a reduced amount of at least one impurity, said method comprising:
    (a) contacting a sample mixture comprising the protein of interest and the at least one impurity to a hydrophobic interaction chromatography (HIC) media in the presence of a load buffer and collecting a flow through fraction, such that the protein of interest binds to the HIC media at a Kp of at least 90; and
    (b) contacting said hydrophobic interaction chromatography media with a wash buffer solution having a salt concentration within 20% of the salt concentration of the load buffer and collecting a wash fraction;
    wherein the flow through and/or wash fractions constitute a preparation comprising a protein of interest and having a reduced amount of the impurity relative to the sample mixture.
2. The method of claim 1, wherein the protein of interest is an immunoglobulin.
3. The method of claim 2, wherein the immunoglobulin comprises the CDRH1, CDRH2, CDRH3, CDRL1, CDRL2 and CDRL3 of adalimumab.
4. A method for producing a preparation comprising adalimumab and a reduced amount of at least one impurity, said method comprising:
    (a) contacting a sample mixture comprising adalimumab and the at least one impurity to a hydrophobic interaction chromatography (HIC) media in the presence of a load buffer and collecting a flow through fraction, such that adalimumab binds to the HIC media at a Kp of at least 90; and
    (b) contacting said hydrophobic interaction chromatography media with a wash buffer solution having a salt concentration within 20% of the salt concentration of the load buffer and collecting a wash fraction;
    wherein the flow through and/or wash fractions constitute a preparation comprising adalimumab and having a reduced amount of the impurity relative to the sample mixture.
5. The method of claim 4, wherein the at least one impurity is an aggregate of adalimumab.
6. The method of claim 5, wherein the aggregate of adalimumab is selected from the group consisting of a multimer, a dimer, a trimer, a tetramer, an oligomer or other high molecular weight species of adalimumab.
7. The method of claim 4, wherein the impurity is a process related impurity.
8. The method of claim 7, wherein the process related impurity is selected from the group consisting of a host cell protein, a host cell nucleic acid, a media component, and a chromatographic material.
9. The method of claim 4, wherein the impurity is a product related substance.
10. The method of claim 9, wherein the product-related substance is selected from the group consisting of a charge variant of adalimumab, an acidic variant species of adalimumab, a basic variant of adalimumab, a lysine variant species of adalimumab, an aggregate of adalimumab, a fragment of adalimumab, an Fc fragment of adalimumab and a Fab fragment of adalimumab.
11. The method of claim 4, wherein the impurity is an acidic species of adalimumab.
12. The method of claim 4, wherein the flow through fraction and the wash fraction are combined.
13. The method of claim 4, wherein the at least one impurity binds to the HIC media at a Kp of greater than 600.
14. The method of claim 4, wherein the hydrophobic interaction chromatography media comprises at least one hydrophobic ligand.
15. The method of claim 14, wherein the at least one hydrophobic ligand is selected from the group consisting of an alkyl-, an aryl-, a butyl, a hexyl, a phenyl, an octyl, and a polypropylene glycol ligand.
16. The method of claim 4, wherein the load buffer and/or wash buffer comprise a salt selected from the group consisting of a sulfate salt, a citrate salt, ammonium sulfate, sodium sulfate, sodium citrate and a combination thereof.
17. The method of claim 4, wherein the total protein load to the column is between 50 and 1000 g/L, between 250 and 700 g/L, or between 350 and 500 g/L.
18. The method of claim 4, wherein prior to subjecting the sample mixture to a hydrophobic interaction chromatography media the sample mixture is subjected to an affinity chromatographic media.
19. The method of claim 4, further comprising subjecting the preparation comprising adalimumab and having a reduced amount of the impurity to an affinity chromatography.
20. The method of claim 18 or 19, wherein the affinity chromatographic media is a Protein A, G, A/G, L or MabSuRe Protein A media.
21. The method of claim 4, wherein prior to subjecting the sample mixture to a hydrophobic interaction chromatography media the sample mixture is subjected to an ion exchange chromatography media.
22. The method of claim 21, further comprising subjecting the preparation comprising adalimumab and having a reduced amount of the impurity to an ion exchange chromatography media.
23. The method of claim 21 or 22, wherein the ion exchange chromatography media is a cation exchange chromatography media or an anion exchange chromatography media.
24. The method of claim 21 or 22, wherein the ion exchange chromatography media is an anion exchange chromatography media selected from media comprising diethylaminoethyl (DEAE), quaternary aminoethyl (QAE) or quaternary amine (Q) group ligands; or wherein the ion exchange chromatography media is a cation exchange chromatography media selected from media comprising carboxymethyl (CM), sulfoethyl(SE), sulfopropyl(SP), phosphate(P) or sulfonate (S) ligands.
25. The method of claim 4, wherein prior to subjecting the sample mixture to a hydrophobic interaction chromatography media the sample mixture is subjected to a mixed mode chromatography media.
26. The method of claim 4, further comprising subjecting the preparation comprising adalimumab and having a reduced amount of the impurity to a mixed mode chromatography media.
27. The method of claim 25 or 26, wherein the mixed mode chromatography media is CaptoAdhere resin.
28. The method of claim 4, wherein prior to subjecting the sample mixture to a hydrophobic interaction chromatography media the sample mixture is subjected to a filtration step.
29. The method of claim 4, further comprising subjecting the preparation comprising adalimumab and having a reduced amount of the impurity to a filtration step.
30. The method of claim 28 or 29, wherein the filtration step is a depth filtration step, a nanofiltration step, an ultrafiltration step, an absolute filtration step, or a combination thereof.

31. The method of claim 4, wherein the HIC media comprises a column.

32. The method of claim 4, wherein the HIC media comprises an agarose media or a membrane functionalized with phenyl groups.

33. The method of claim 4, wherein the wash buffer is identical to the load buffer.

34. The method of claim 4, wherein the at least one impurity is reduced by at least 65%, 77% or 87% relative to the sample mixture.

35. The method of claim 4, wherein the Kd for the binding of adalimumab to the HIC media is at least 0.47.

36. The method of claim 4, wherein the Kd for the binding of the at least one impurity to the HIC media is less than or equal to 0.01.

37. The method of claim 4, wherein adalimumab has a Qmax of at least 41.

38. The method of claim 4, wherein the at least one impurity has a Qmax of at least 6.

39. The method of claim 4, wherein the load buffer and/or the wash buffer has a salt concentration in the range of 80 mM-1000 mM.

40. The method of claim 4, wherein the load buffer and/or wash buffer comprise a cation selected from the group consisting of $Ba^{2+}$; $Ca^{2+}$; $Mg^{2+}$; $Li^+$; $Cs^+$; $Na^+$; $K^+$; $Rb^+$; $NH_4^+$ and a combination thereof.

41. The method of claim 4, wherein the load buffer and/or wash buffer comprise an anion selected from the group consisting of $PO_4^{3-}$; $SO_4^{2-}$; $CH_3CO_3^-$; $Cl^-$; $Br^-$; $NO_3^-$; $ClO_4^-$; $I^-$; $SCN^-$ and a combination thereof.

42. The method of claim 4, wherein the sample mixture has an adalimumab concentration of between 0.5 and 30 g/L, between 1 and 20 g/L, or between 3 and 10 g/L.

43. The method of claim 4, wherein the impurity is reduced to a level of 0.5 to 0.1 g/L, 0.1 to 0.05 g/L or below 0.05 g/L.

44. The method of claim 4, wherein the sample mixture is subjected to the hydrophobic interaction media at a pH range of 5-8.5.

45. The method of claim 4, wherein the at least one impurity bound to the HIC media remains bound upon washing with the wash buffer.

* * * * *